United States Patent
Yamada et al.

(10) Patent No.: US 7,396,899 B2
(45) Date of Patent: Jul. 8, 2008

(54) CHEMICAL AMPLIFICATION TYPE RESIST COMPOSITION

(75) Inventors: Airi Yamada, Ibaraki (JP); Yasunori Uetani, Tsukuba (JP); Akira Kamabuchi, Ashiya (JP)

(73) Assignee: Sumitomo Chemical Co., Ltd., Osaka (JP)

(*) Notice: Subject to any disclaimer, the term of this patent is extended or adjusted under 35 U.S.C. 154(b) by 0 days.

(21) Appl. No.: 11/643,662

(22) Filed: Dec. 22, 2006

(65) Prior Publication Data

US 2007/0123674 A1 May 31, 2007

Related U.S. Application Data

(62) Division of application No. 10/682,038, filed on Oct. 10, 2003, now Pat. No. 7,160,669.

(30) Foreign Application Priority Data

Oct. 16, 2002 (JP) ............................. 2002-301517

(51) Int. Cl.
G03F 7/039 (2006.01)
C08G 73/00 (2006.01)

(52) U.S. Cl. ................. 528/373; 430/285.1; 430/281.1; 430/270.1; 430/921; 430/922; 430/914

(58) Field of Classification Search ................. 528/373; 430/285.1, 270.1, 281.1, 921, 922, 914
See application file for complete search history.

(56) References Cited

U.S. PATENT DOCUMENTS

| | | | |
|---|---|---|---|
| 4,061,867 A * | 12/1977 | Hamsher | 560/219 |
| 5,101,053 A * | 3/1992 | Boettcher | 556/64 |
| 5,691,111 A | 11/1997 | Iwas et al. | |
| 2001/0014428 A1 | 8/2001 | Uetani et al. | |
| 2003/0219647 A1 * | 11/2003 | Wariishi | 429/111 |
| 2003/0224284 A1 | 12/2003 | Tao | |
| 2005/0019689 A1 | 1/2005 | Kodama | |

FOREIGN PATENT DOCUMENTS

JP 11-228534 A 8/1999

JP 11228534 A * 8/1999

OTHER PUBLICATIONS

Derwent-AccNo: 1966-136264, Derwent-Week: 199831, Hasegawa et al, Patent Family inclusive of JP08027102 A and US5691111 A, two pages printed out Feb. 5, 2006 from East, Derwent Database.

* cited by examiner

Primary Examiner—Randy Gulakowski
Assistant Examiner—Alicia M Toscano
(74) Attorney, Agent, or Firm—Birch, Stewart, Kolasch & Birch, LLP

(57) ABSTRACT

The present invention provides a sulfonium salt of the formula (Ia)

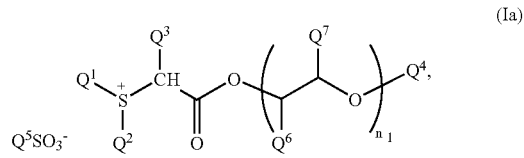

a polymeric compound comprising a structural unit of the formula (Ib)

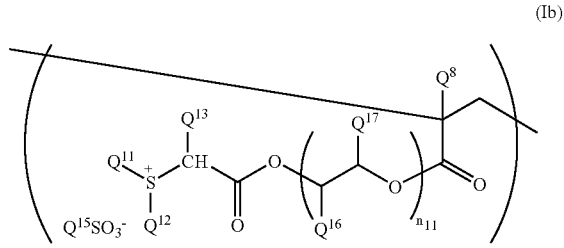

and a chemical amplification type positive resist composition comprising (A) an acid generator comprising at least one compound selected from the group consisting of a sulfonium salt of the formula (Ia), a polymeric compound comprising a structural unit of the formula (Ib), and a sulfonium salt of the formula (Ic); and
(B) resin which contains a structural unit having an acid labile group and which itself is insoluble or poorly soluble in an alkali aqueous solution but becomes soluble in an alkali aqueous solution by the action of an acid.

3 Claims, No Drawings

CHEMICAL AMPLIFICATION TYPE RESIST COMPOSITION

CROSS-REFERENCE TO RELATED APPLICATIONS

The present application is a 37 C.F.R. § 1.53(b) divisional of U.S. application Ser. No. 10/682,038 filed Oct. 10, 2003, now U.S. Pat. No. 7,160,669 which in turn claims priority on Japanese Application No. 2002-301517 filed Oct. 16, 2002. The entire contents of each of these applications are hereby incorporated by reference.

BACKGROUND OF THE INVENTION

1. Field of the Invention

The present invention relates to a chemical amplification type resist composition for use in microfabrication of semiconductor.

2. Related Art

Semiconductor microfabrication employs a lithography process using a resist composition. In lithography, theoretically, the shorter the exposure wavelength becomes, the higher the resolution can be made, as expressed by Rayleigh's diffraction limit formula. The wavelength of an exposure light source for lithography used in the manufacture of semiconductor devices has been shortened year by year as g line having a wavelength of 436 nm, i line having a wavelength of 365 nm, KrF excimer laser having a wavelength of 248 nm and ArF excimer laser having a wavelength of 193 nm. $F_2$ excimer laser having a wavelength of 157 nm seems to be promising as the next-generation exposure light source. Further, as the exposure light source of the subsequent generation, soft X ray (EUV) having a wavelength of 13 nm or shorter has been proposed as the exposure light source following the 157 nm-wavelength $F_2$ excimer laser.

Since light sources having shorter wavelength than that of g line and i line, such as excimer laser and the like have low illumination, it is necessary to enhance the sensitivity of a resist. Consequently, there are used so-called chemical amplification type resists utilizing the catalytic action of an acid produced from a sulfonium salt and the like by exposure and containing a resin having a group being dissociated by this acid.

However, in conventionally known chemical amplification type resist compositions, there is a problem that line edge roughness occurs by generation of standing wave and the like, namely, smoothness on a pattern side wall decreases, and resultantly, uniformity of line width deteriorates and collapse of the patterns occurs due to its adhesivity with substrate.

SUMMARY OF THE INVENTION

An object of the present invention is to provide a chemical amplification type positive resist composition suitable for excimer laser lithography using ArF, KrF and the like, showing excellent various resist abilities such as sensitivity, resolution and the like, and particularly to provide the resist composition giving stable fine patterns without collapse as well as giving improved line edge roughness.

The present invention relates to the followings:

<1> A sulfonium salt of the formula (Ia)

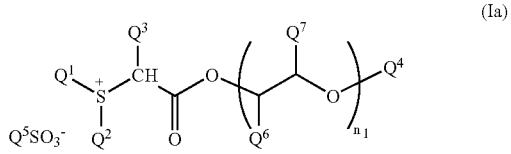

(Ia)

wherein $Q^1$ and $Q^2$ each independently represent alkyl having 1 to 6 carbon atoms or cycloalkyl having 3 to 10 carbon atoms, or $Q^1$ and $Q^2$ bond to form divalent acyclic hydrocarbon having 3 to 7 carbon atoms which form a ring together with the adjacent $S^+$; $Q^3$, $Q^6$ and $Q^7$ each independently represent hydrogen or methyl; $Q^4$ represents a group of the formula (X)

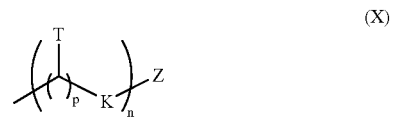

(X)

wherein T represents hydrogen, alkyl having 1 to 10 carbon atoms or cycloalkyl having 3 to 10 carbon atoms, Z represents hydrogen, alkyl having 1 to 10 carbon atoms or cycloalkyl having 3 to 10 carbon atoms, K represents a divalent group selected from the group consisting of the following formulae

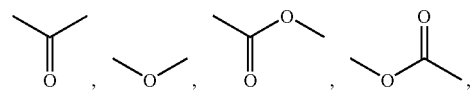

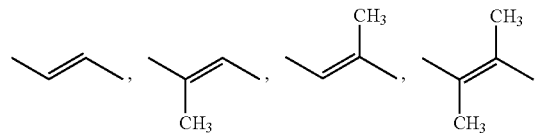

n denotes an integer of from 0 to 10, and p denotes an integer of from 0 to 3, when n or p is 2 or more, each T may be the same or different and when n is 2 or more, each K may be the same or different;

$n_1$ denotes 0 or natural number; and $Q^5$ represents perfluoroalkyl having 1 to 8 carbon atoms, alkyl having 1 to 8 carbon atoms or aromatic group having 6 to 12 carbon atoms which may be substituted; or camphor group;

with the proviso that when $n_1$ denotes 0, n denotes an integer of from 1 to 10, and when $n_1$ denotes 1 and n denotes 0, Z is not alkyl.

<2> A polymeric compound comprising a structural unit of the formula (Ib)

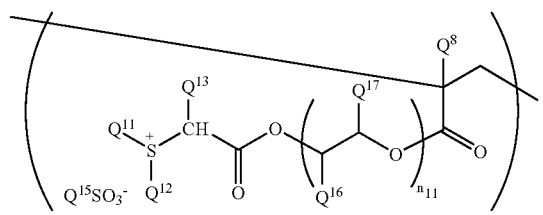
(Ib)

wherein $Q^{11}$ and $Q^{12}$ each independently represent alkyl having 1 to 6 carbon atoms or cycloalkyl having 3 to 10 carbon atoms, or $Q^{11}$ and $Q^{12}$ bond to form divalent acyclic hydrocarbon having 3 to 7 carbon atoms which form a ring together with the adjacent $S^+$; $Q^8$, $Q^{13}$, $Q^{16}$ and $Q^{17}$ each independently represent hydrogen or methyl; $n_{11}$ denotes 0 or natural number; and $Q^{15}$ represents perfluoroalkyl having 1 to 8 carbon atoms, alkyl having 1 to 8 carbon atoms or aromatic group having 6 to 12 carbon atoms which may be substituted, or camphor group.

<3> A chemical amplification type positive resist composition comprising (A) an acid generator comprising at least one compound selected from the group consisting of a sulfonium salt of the formula (Ia), a polymeric compound comprising a structural unit of the formula (Ib), and a sulfonium salt of the formula (Ic)

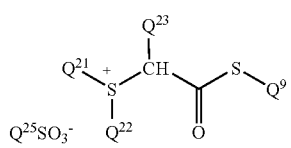
(Ic)

wherein $Q^{21}$ and $Q^{22}$ each independently represent alkyl having 1 to 6 carbon atoms or cycloalkyl having 3 to 10 carbon atoms, or $Q^{21}$ and $Q^{22}$ bond to form divalent acyclic hydrocarbon having 3 to 7 carbon atoms which form a ring together with the adjacent $S^+$, $Q^{23}$ represents hydrogen or methyl, $Q^9$ represents a group of the formula $(X^1)$

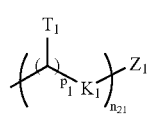
$(X^1)$ wherein $T_1$ represents hydrogen, alkyl having 1 to 10 carbon atoms or cycloalkyl having 3 to 10 carbon atoms, $Z_1$ represents hydrogen, alkyl having 1 to 10 carbon atoms or cycloalkyl having 3 to 10 carbon atoms, $K_1$ represents a divalent group selected from the group consisting of the following formulae

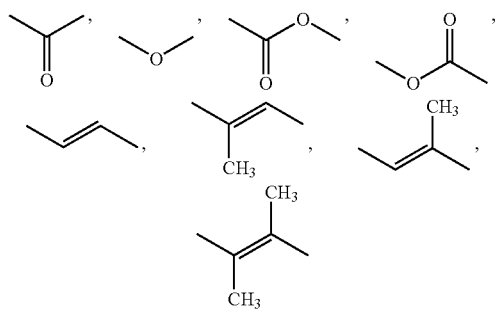

$n_{21}$ denotes an integer of from 0 to 10, $p_1$ denotes an integer of from 0 to 3, when $n_{21}$ or $p_1$ is 2 or more, each $T_1$ may be the same or different and when $n_{21}$ is 2 or more, each $K_1$ may be the same or different, $Q^{25}$ represents perfluoroalkyl having 1 to 8 carbon atoms, alkyl having 1 to 8 carbon atoms or aromatic group having 6 to 12 carbon atoms which may be substituted, or camphor group, and (B) resin which contains a structural unit having an acid labile group and which itself is insoluble or poorly soluble in an alkali aqueous solution but becomes soluble in an alkali aqueous solution by the action of an acid.

<4> The composition according to <3> wherein the acid generator further comprises at least one compound selected from the group consisting of triphenylsulfonium salt of the formula (IVa)

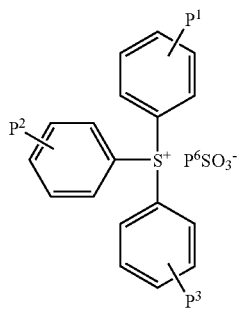
(IVa)

wherein $P^1$, $P^2$ and $P^3$ each independently represent hydrogen, hydroxyl, alkyl having 1 to 6 carbon atoms or alkoxy having 1 to 6 carbon atoms; and $P^6SO_3^{31}$ represents organic sulfonate ion, and diphenyliodonium salt of the formula (IVb)

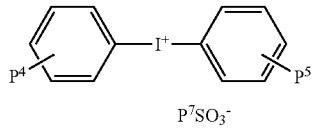
(IVb)

wherein $P^4$ and $P^5$ each independently represent hydrogen, hydroxyl, alkyl having 1 to 6 carbon atoms or alkoxy having 1 to 6 carbon atoms; and $P^7SO_3^-$ represents organic sulfonate ion.

<5> The composition according to <3> or <4> wherein $Q^4$ and $Q^9$ is the ones having at least one ethylenically unsaturated bond.

<6> The composition according to <3> or <4> wherein $Q^9$ is the one of the formula (II).

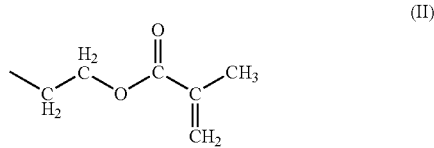
(II)

<7> The composition according to any one of <3> to <6> wherein the content of the structural unit having an acid labile group is 10 to 80% by mol in the resin.

<8> The compound according to any one of <3> to <7> wherein the structural unit having an acid labile group is the one derived from at least one monomer selected from the group consisting of 2-alkyl-2-adamantyl (meth)acrylate, and 3-hydroxy-1-adamantyl(meth)acrylate.

<9> The composition according to any one of <3> to <8> wherein the resin further contains, in addition to the structural unit having the acid-labile group, at least one structural unit selected from the group consisting of a structural unit derived from 3-hydroxy-1-adamantyl(meth)acrylate, a structural unit derived from 3,5-dihydroxy-1-adamantyl(meth)acrylate, a structural unit derived from (meth)acryloyloxy-γ-butyrolactone having a lactone ring optionally substituted by alkyl, a structural unit of the formula (IIIa) and a structural unit of the following formula (IIIb)

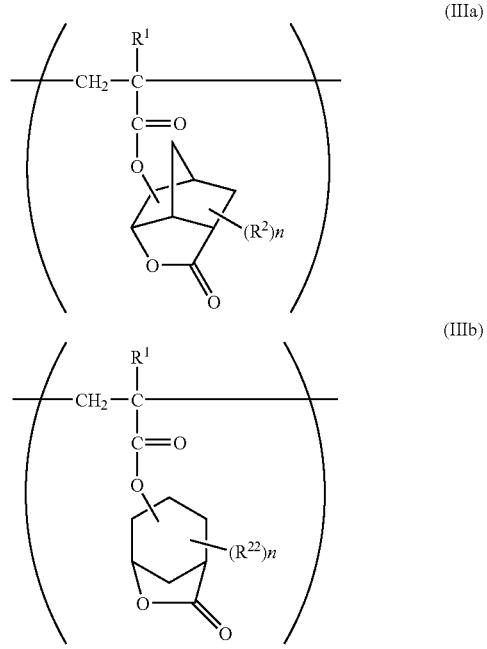

wherein $R^1$ and $R^{21}$ each independently represent hydrogen, methyl or trifluoromethyl, and $R^2$ and $R^{22}$ each independently represent methyl or trifluoromethyl, and n denotes an integer of from 1 to 3.

<10> The composition according to any of <3> to <9> wherein the resin further contains a structural unit derived from 2-norbornene and a structural unit derived from an aliphatic unsaturated dicarboxylic anhydride.

<11> The composition according to <10> wherein the structural unit derived from 2-norbornene is a structural unit of the formula (VI)

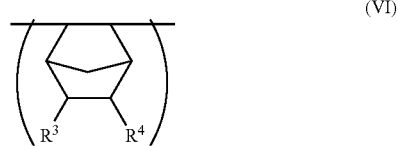
(VI)

wherein $R^3$ and $R^4$ each independently represent hydrogen, alkyl having 1 to 3 carbon atoms, hydroxyalkyl having 1 to 3 carbon atoms, carboxyl, cyano or —COOG group in which G represents alcohol residue, or $R^3$ and $R^4$ bond together to form a carboxylic anhydride residue represented by —C(=O)OC(=O)—; and the structural unit derived from the aliphatic unsaturated dicarboxylic anhydride is at least one structural unit selected from the group consisting of the formulae (VII) and (VIII).

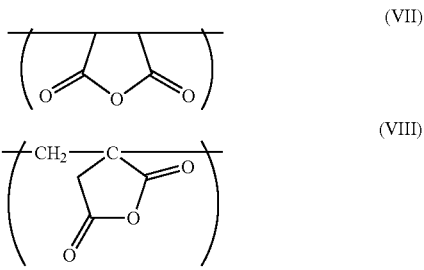

<12> The composition according to any one of <3> to <11> which further comprises basic nitrogen-containing organic compound as a quencher.

DESCRIPTION OF PREFERRED EMBODIMENTS

In the sulfonium salt of the formula (Ia) (hereinafter referred to as "Salt (Ia)"), $Q^1$ and $Q^2$ each independently represent alkyl having 1 to 6 carbon atoms or cycloalkyl having 3 to 10 carbon atoms, or $Q^1$ and $Q^2$ bond to form divalent acyclic hydrocarbon having 3 to 7 carbon atoms which forms a ring together with the adjacent $S^+$. Specific examples of the alkyl and cycloalkyl include methyl, ethyl, propyl, isopropyl, butyl, tert-butyl, pentyl, hexyl, cyclohexyl, and the like. Specific examples of the ring group formed by adjacent $S^+$ and divalent acyclic hydrocarbon by $Q^1$ and $Q^2$ include tetramethylenesulfonio group, oxybisethylenesulfonio group, thiobisethylenesulfonio group, carbonybisethylenesulfonio group, carbonylmethyleneethylenesulfonio group, and the like.

$Q^3$, $Q^6$ and $Q^7$ each independently represent hydrogen or methyl.

$n_1$ denotes 0 or natural number, and preferably 0 to 5, more preferably 0 to 3.

$Q^4$ represents a group of the formula (X)

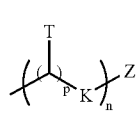 (X)

wherein T represents hydrogen, alkyl having 1 to 10 carbon atoms or cycloalkyl having 3 to 10 carbon atoms, Z represents hydrogen, alkyl having 1 to 10 carbon atoms or cycloalkyl having 3 to 10 carbon atoms, K represents a divalent group selected from the group consisting of the following formulae

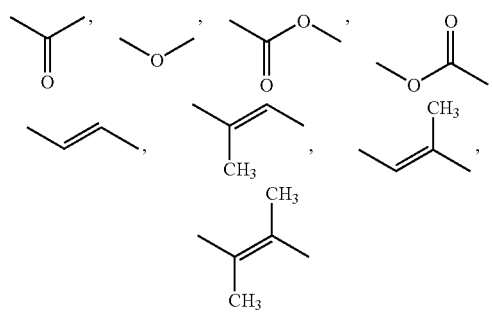

n denotes an integer of from 0 to 10, p denotes an integer of from 0 to 3, when n or p is 2 or more, each T may be the same or different and when n is 2 or more, each K may be the same or different.

Examples of $Q^4$ includes alkylcarbonyloxy, alkoxycarbonyl, acryloyloxyalkoxycarbonyl, methacryloxyalkoxycarbonyl, alkenyl, alkenylcarbonyloxy, alkenylcarbonyloxyalkyl, alkenylcarbonyloxyalkyloxy, alkenylcarbonyloxyalkyloxycarbonyl, and the like. As $Q^4$, the ones having at least one ethylenically unsaturated bond are preferred.

$Q^5$ represents perfluoroalkyl having 1 to 8 carbon atoms, alkyl having 1 to 8 carbon atoms or aromatic group having 6 to 12 carbon atoms which may be substituted, or camphor group. Specific examples of the perfluoroalkyl include trifluoromethyl, perfluorobutyl, perfluorooctyl, and the like. Specific examples of the alkyl include methyl, ethyl, propyl, isopropyl, butyl, pentyl, hexyl, cyclohexyl, octyl, and the like. Specific examples of the aromatic ring group which may be substituted include phenyl, tolyl, xylyl, mesityl, naphtyl, and the like.

In the formula (Ia), when $n_1$ denotes 0; n is an integer of 1 to 10, and when $n_1$ is 1 and n denotes 0, Z is not alkyl.

Salt (Ia) can be produced according to known method, such as the method described in J. Polymer Science., Polymer Chemistry Edition, Vol. 17, 2877-2892 (1979) written by J. V. Crivello et al., or the method described in J. Am. Chem. Soc., Vol. 108, 1579-1585 (1986) written by D. N. Kevill et al.

Specific examples of cation of Salt (Ia) include the followings:

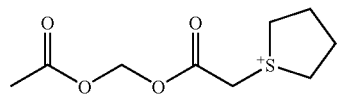

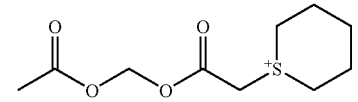
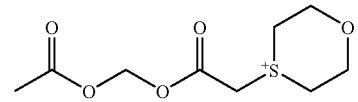
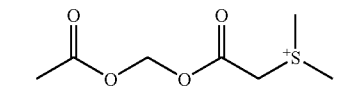
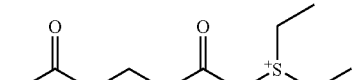
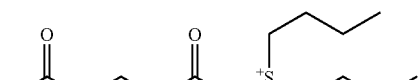
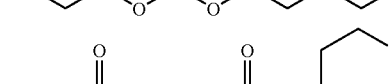
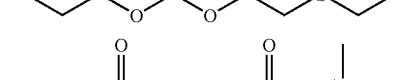
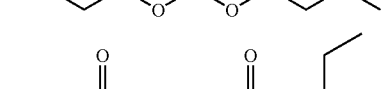
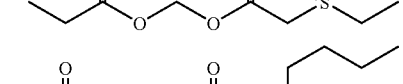
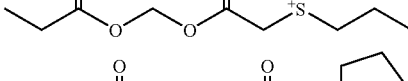
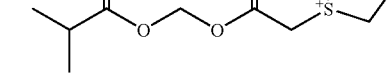
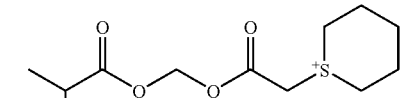
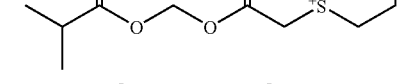
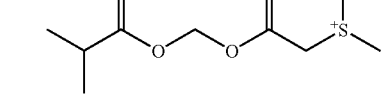

-continued
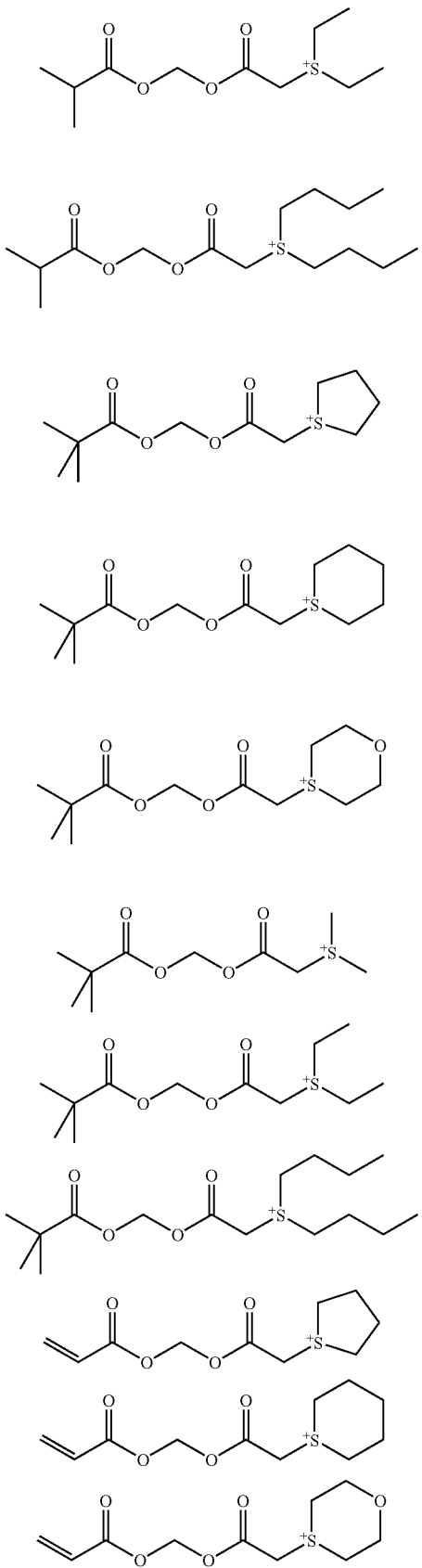
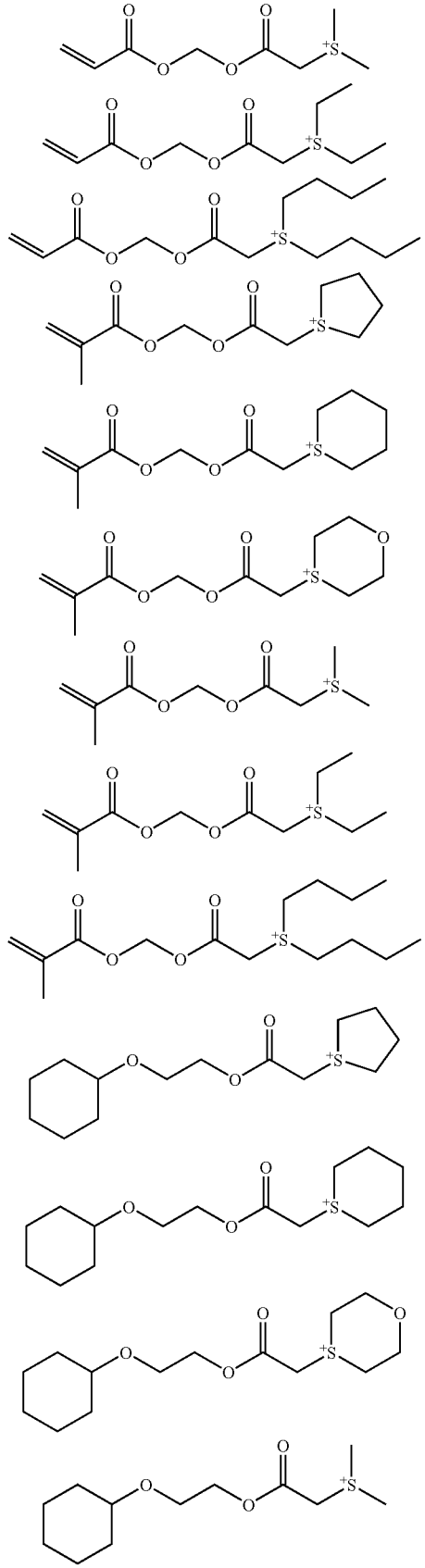

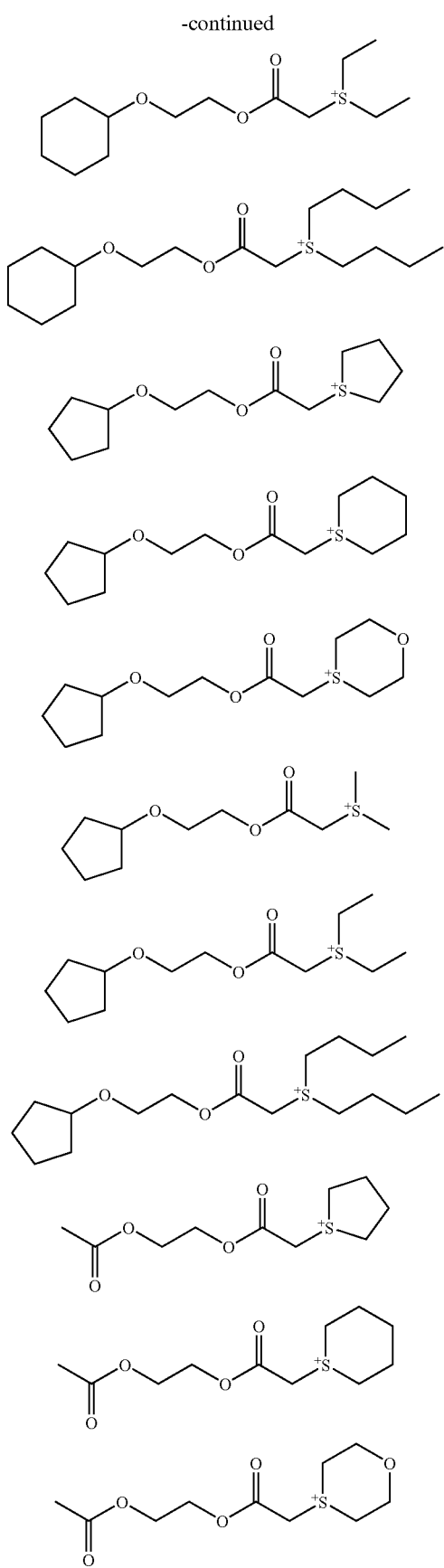
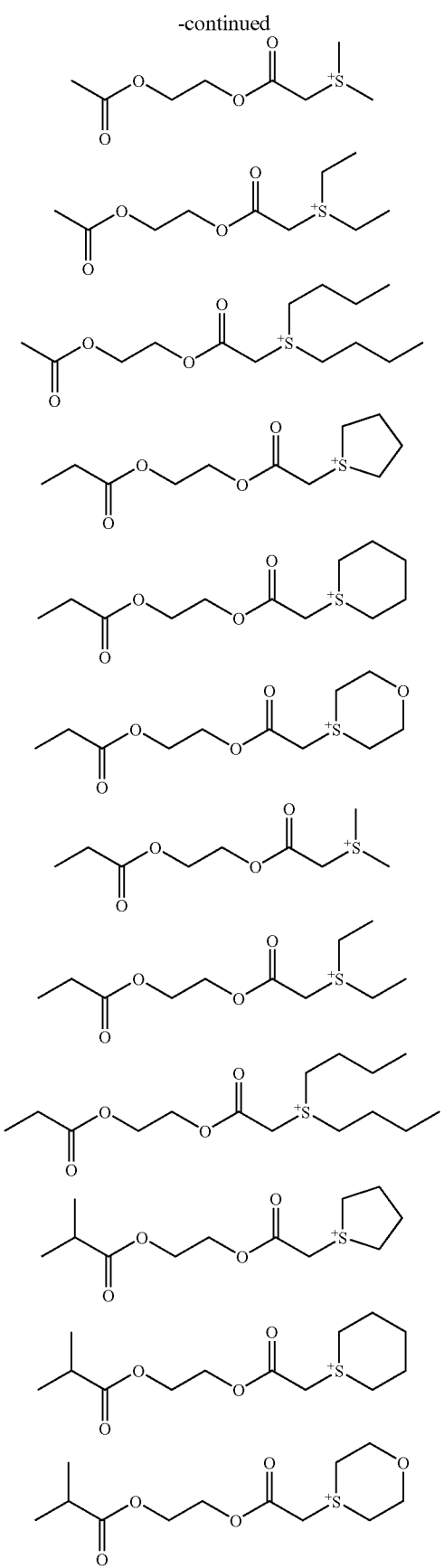

-continued
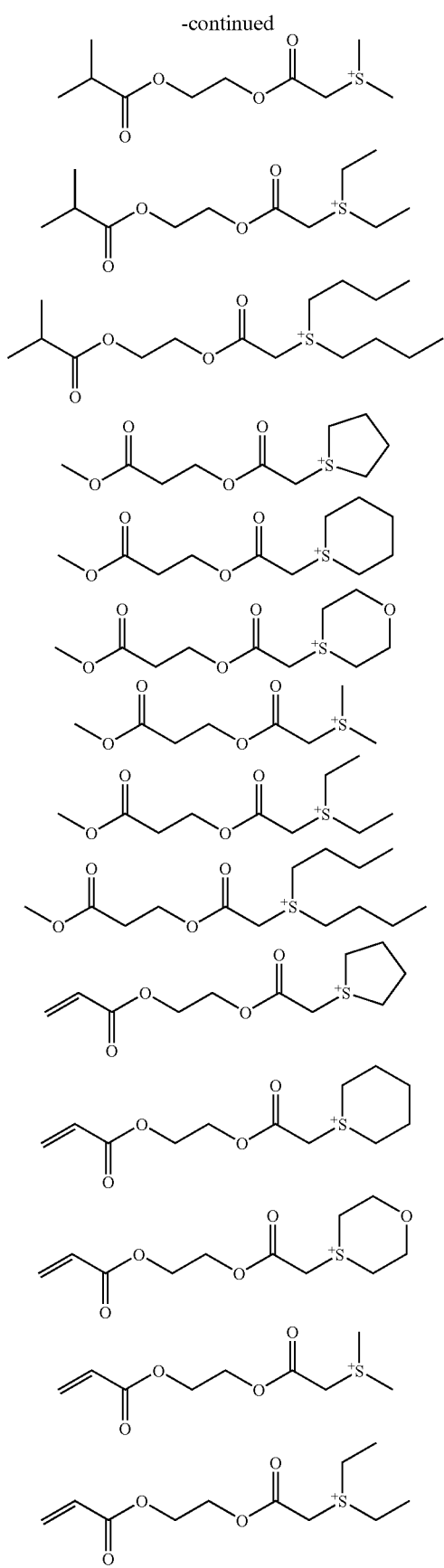
-continued
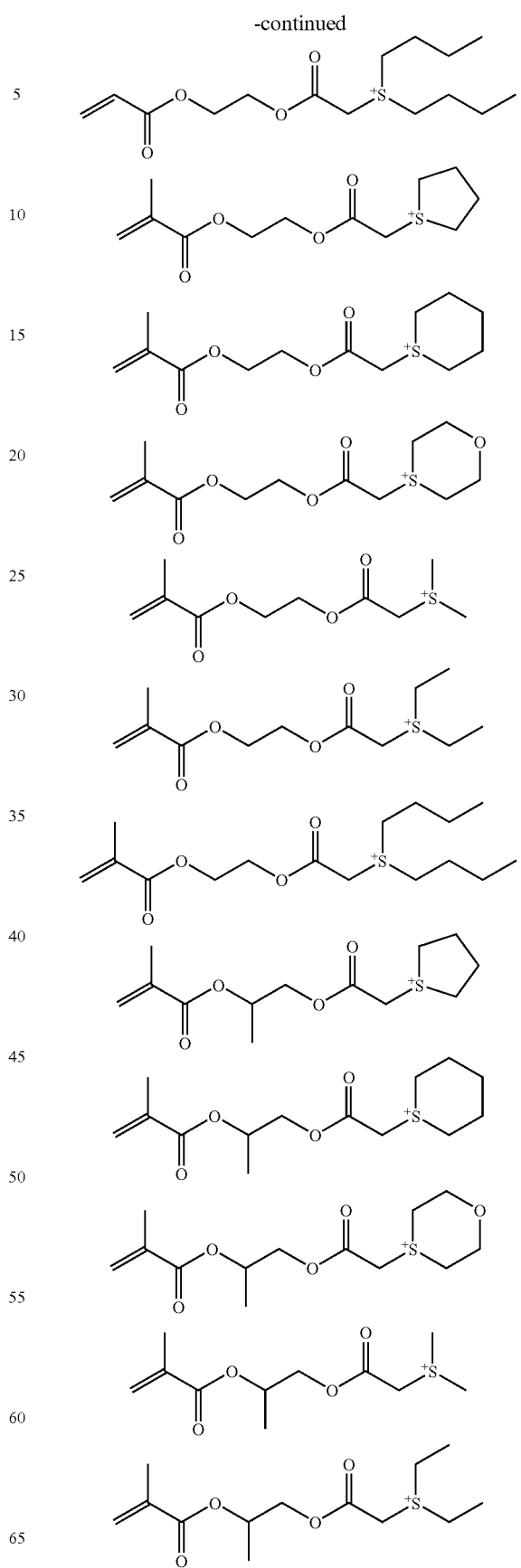

-continued
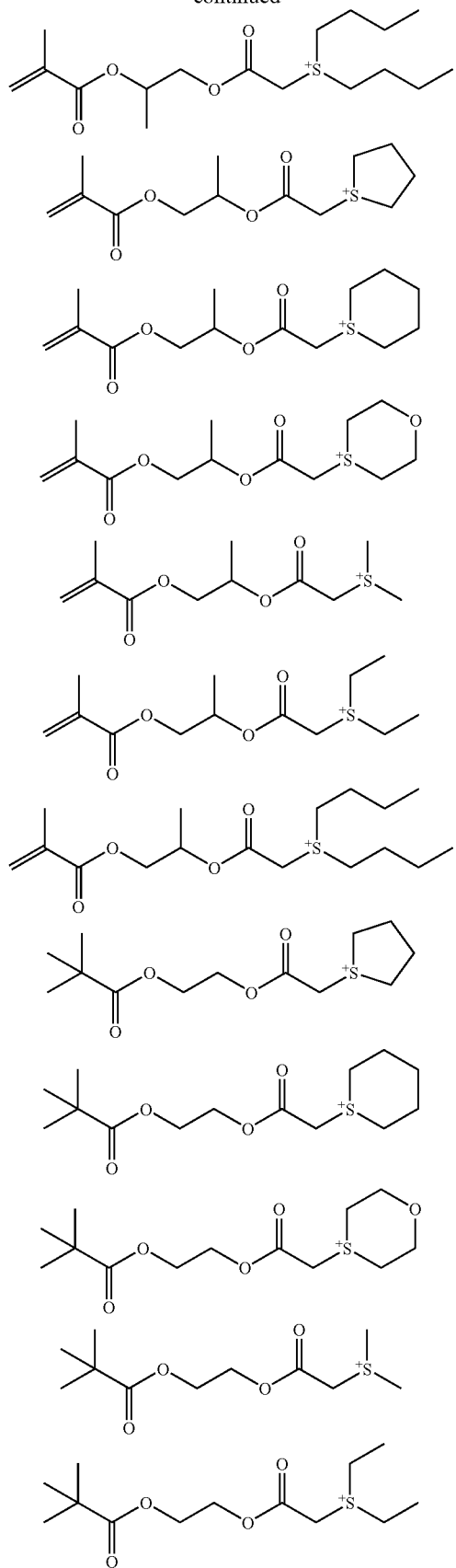
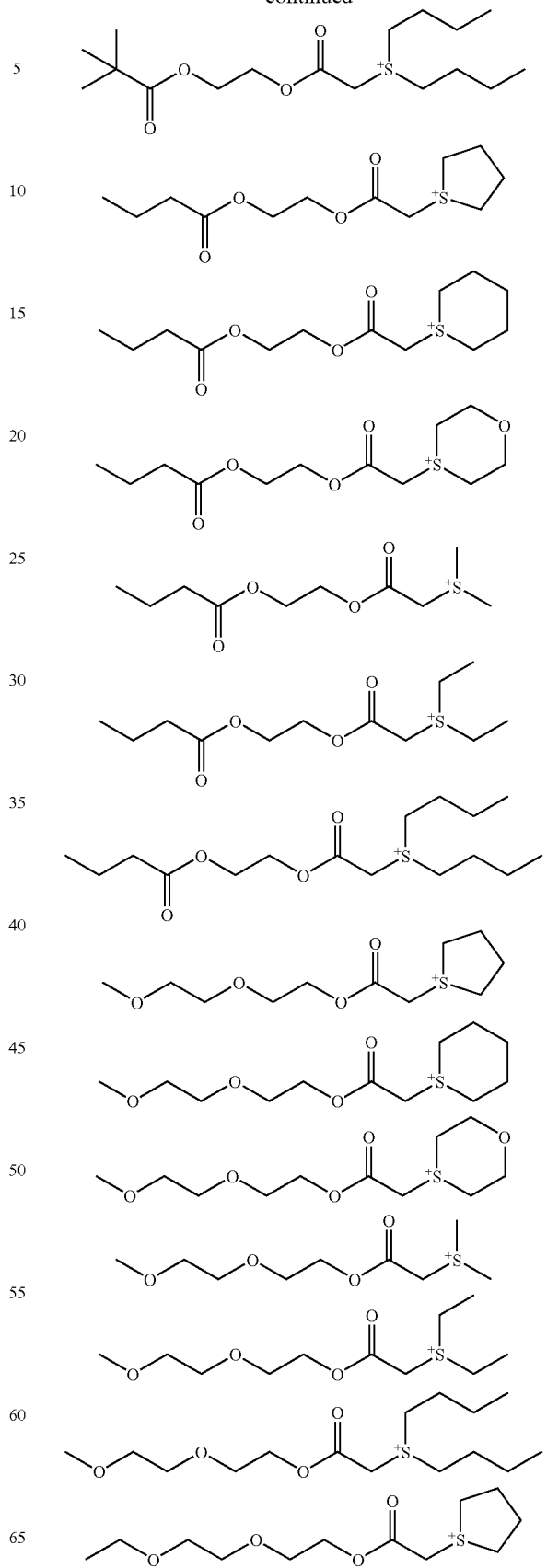

-continued
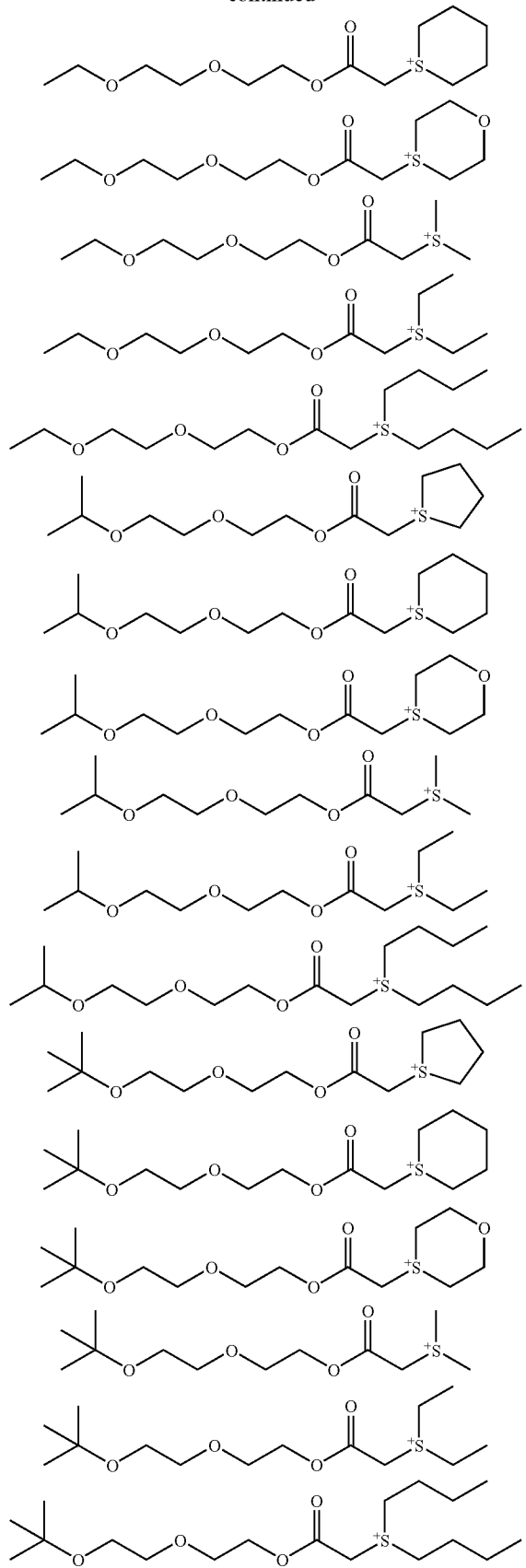
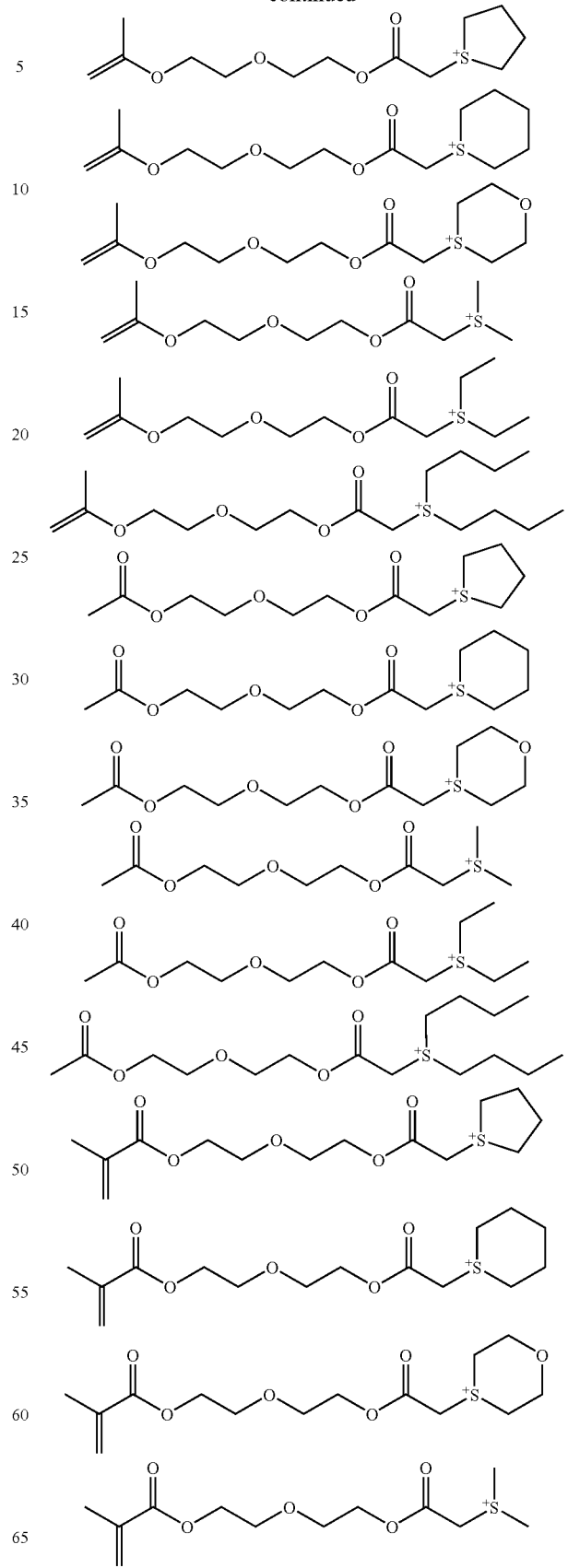

-continued
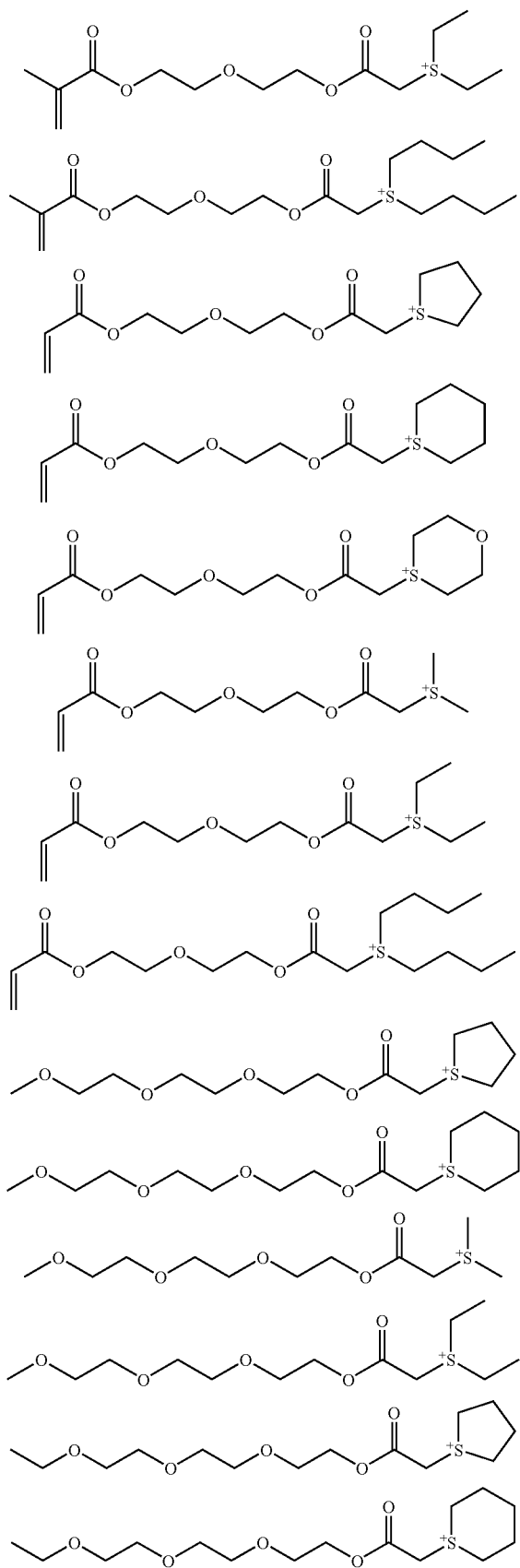
-continued
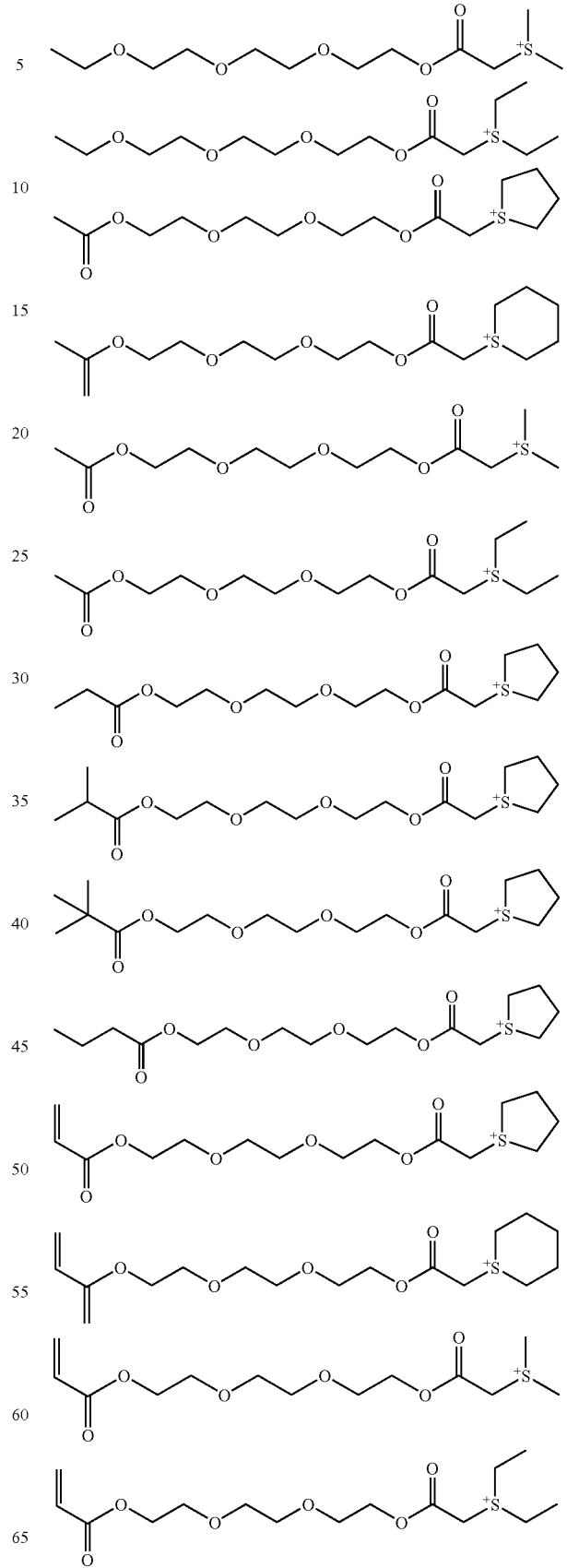

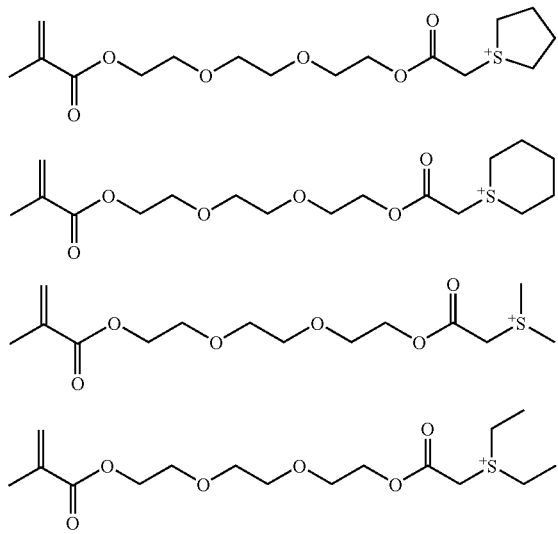

Specific examples of anion of Salt (Ia) represented by $Q^5SO_3^-$ include methanesulfonate, ethanesulfonate, butanesulfonate, butanesulfonate, trifluoromethanesulfonate, perfluorobutanesulfonate, perfluorooctanesulfonate, p-toluenesulfonate, camphorsulfonate, and the like.

In the sulfonium salt of the formula (Ic) (hereinafter referred to as "Salt (Ic)"), $Q^{21}$ and $Q^{22}$ each independently represent alkyl having 1 to 6 carbon atoms or cycloalkyl having 3 to 10 carbon atoms, or $Q^{21}$ and $Q^{22}$ bond to form divalent acyclic hydrocarbon having 3 to 7 carbon atoms which forms a ring together with the adjacent $S^+$. Examples of $Q^{21}$ and $Q^{22}$ include the same as exemplified in $Q^1$ and $Q^2$ in the formula (Ia).

$Q^{23}$ represents hydrogen or methyl.

$Q^9$ represents a group of the formula ($X^1$)

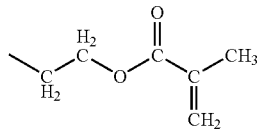

wherein $T_1$ represents hydrogen, alkyl having 1 to 10 carbon atoms or cycloalkyl having 3 to 10 carbon atoms, $Z_1$ represents hydrogen, alkyl having 1 to 10 carbon atoms or cycloalkyl having 3 to 10 carbon atoms, $K_1$ represents a divalent group selected from the group consisting of the following formulae

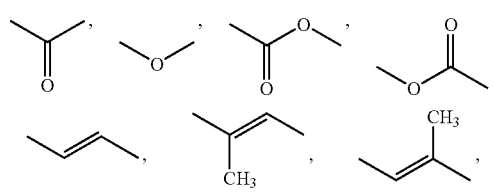

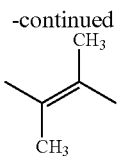

$n_{21}$ denotes an integer of from 0 to 10, $p_1$ denotes an integer of from 0 to 3, when $n_{21}$ or $p_1$ is 2 or more, each $T_1$ may be the same or different and when $n_{21}$ is 2 or more, each $K_1$ may be the same or different. Examples of $Q^9$ includes alkylcarbonyloxy, alkoxycarbonyl, acryloyloxyalkoxycarbonyl, methacryloyloxyalkoxycarbonyl, alkenyl, alkenylcarbonyloxy, alkenylcarbonyloxyalkyl, alkenylcarbonyloxyalkyloxy, alkenylcarbonyloxyalkyloxycarbonyl, and the like. As $Q^9$, the ones having at least one ethylenically unsaturated bond are preferred and the one of the following formula (II) is more preferred.

(II)

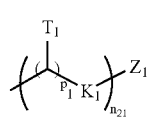

$Q^{25}$ represents perfluoroalkyl having 1 to 8 carbon atoms, alkyl having 1 to 8 carbon atoms or aromatic group having 6 to 12 carbon atoms which may be substituted; or camphor group. Examples of $Q^{25}$ include the same as exemplified in $Q^5$ in the formula (Ia).

Salt (Ic) can be produced according to known method, such as the method described in J. Polymer Science., Polymer Chemistry Edition, Vol. 17, 2877-2892 (1979) written by J. V. Crivello et al., or the method described in J. Am. Chem. Soc., Vol. 108, 1579-1585 (1986) written by D. N. Kevill et al.

Specific examples of Salt (Ic) include the followings:

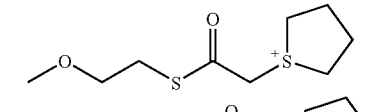

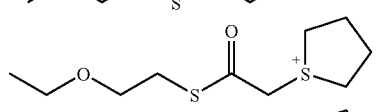

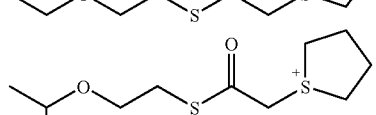

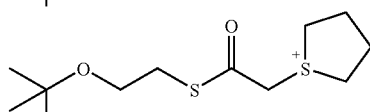

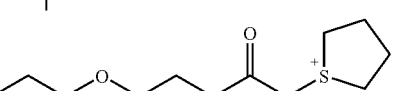

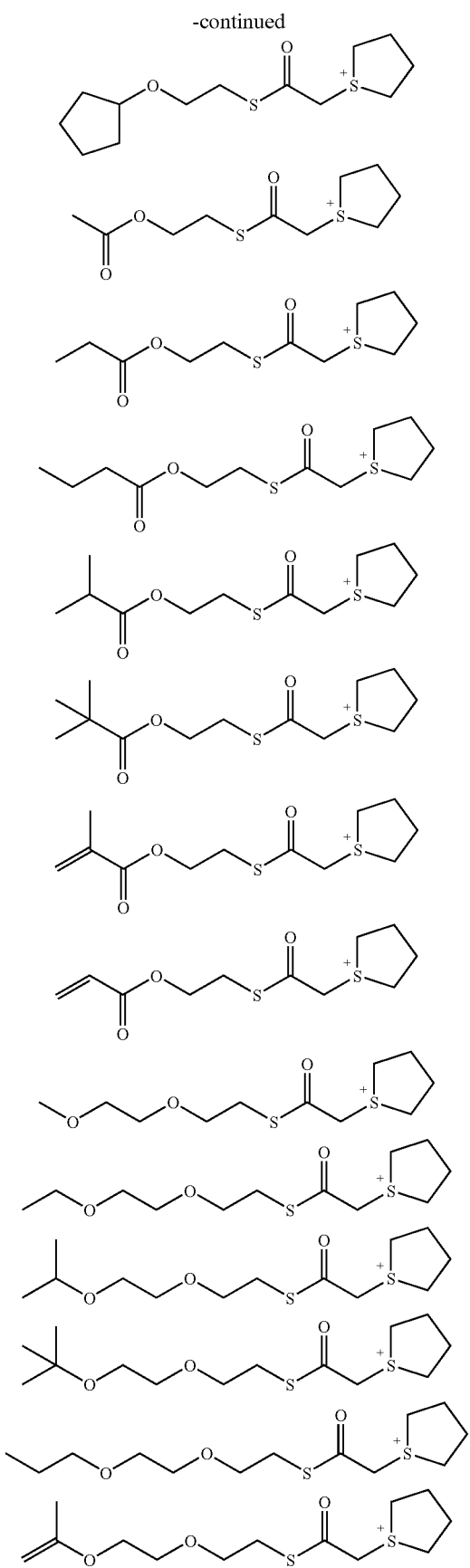
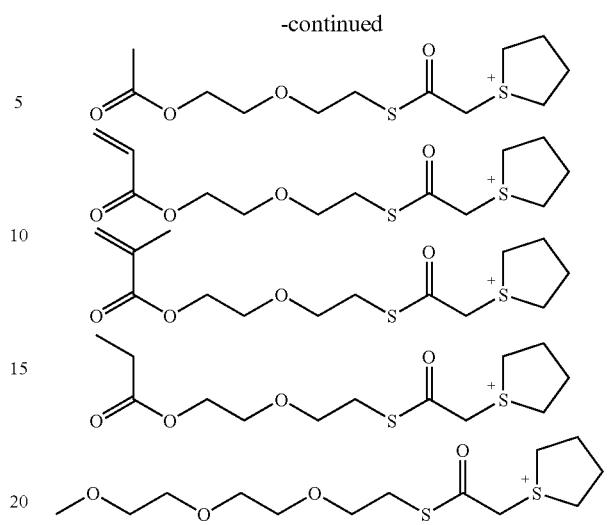

In the polymeric compound comprising a structural unit of the formula (Ib) (hereinafter referred to as "Polymer (Ib)"), $Q^{11}$ and $Q^{12}$ each independently represent alkyl having 1 to 6 carbon atoms or cycloalkyl having 3 to 10 carbon atoms, or $Q^{11}$ and $Q^{12}$ bond to form divalent acyclic hydrocarbon having 3 to 7 carbon atoms which forms a ring together with the adjacent $S^+$. Examples of $Q^{11}$ and $Q^{12}$ include the same as exemplified in $Q^1$ and $Q^2$ in the formula (Ia).

$Q^{13}$, $Q^{16}$, $Q^{17}$ and $Q^8$ each independently represent hydrogen or methyl.

$n_{11}$ denotes 0 or natural number, and preferably 0 to 5, more preferably 0 to 3.

$Q^{15}$ represents perfluoroalkyl having 1 to 8 carbon atoms, alkyl having 1 to 8 carbon atoms or aromatic group having 6 to 12 carbon atoms which may be substituted; or camphor group. Examples of $Q^{15}$ include the same as exemplified in $Q^5$ in the formula (Ia).

Polymer (Ib) can be produced by polymerizing Salt (Ia) or Salt (Ic) having ethylenically unsaturated bond by conventional radical polymerization. The conventional radical polymerization is the polymer obtaining method by mixing a radical initiator such as diazonium compound and acyl peroxide which is easily decomposed to produce radical, and a compound having ethylenically unsaturated bond in a solvent. As the radical initiator, azobisisobutyronitrile, benzoyl peroxide, and the like may be usually used.

The chemical amplification type positive resist composition of the present invention (hereinafter referred to as "the present composition") comprises (A) an acid generator comprising at least one acid generator selected from the group consisting of Salt (Ia), Polymer (Ib) and Salt (Ic); and (B) resin which contains a structural unit having an acid labile group and which itself is insoluble or poorly soluble in an alkali aqueous solution but becomes soluble in an alkali aqueous solution by the action of an acid.

As better sensitivity and resolution of the resist can be obtained, it is preferable that at least one onium salt selected from the group consisting of triphenylsulfonium salt of the formula (IVa) and diphenylsulfonium salt of the formula (IVb) is contained in the present composition in addition to at least one compound selected from the group consisting of Salt (Ia), Polymer (Ib) and Salt (Ic).

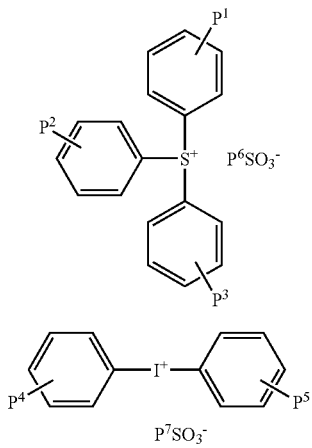

(IVa)

(IVb)

In the formula (IVa), $P^1$, $P^2$ and $P^3$ each independently represent hydrogen, hydroxyl, alkyl having 1 to 6 carbon atoms or alkoxy having 1 to 6 carbon atoms, and the alkyl and alkoxy may be linear or branched in the case of 3 or more carbon atoms.

In the formula (IVb), $P^4$ and $P^5$ each independently represent hydrogen, hydroxyl, alkyl having 1 to 6 carbon atoms or alkoxy having 1 to 6 carbon atoms, and the alkyl and alkoxy may be linear or branched in the case of 3 or more carbon atoms.

In $P^1$, $P^2$, $P^3$, $P^4$ and $P^5$, specific examples of the alkyl include methyl, ethyl, propyl, isopropyl, butyl, tert-butyl, pentyl, hexyl and the like, and examples of the alkoxy include methoxy, ethoxy, propoxy, butoxy and the like.

$P^6SO_3^-$ in the formula (IVa) and $P^7SO_3^-$ in the formula (IVb) each independently represent organic sulfonate ion. $P^6$ and $P^7$ may be an organic group having 1 to about 12 carbon atoms. Examples thereof include alkyl having 1 to 8 carbon atoms such as methyl, ethyl, propyl, isopropyl, butyl, pentyl, hexyl, heptyl, and the like; perfluoroalkyl having 1 to 8 carbon atoms such as trifluoromethyl, perfluorobuthyl, perfluorooctyl, and the like; cycloalkyl such as cyclopentyl, cyclohexyl, and the like; aromatic group having 6 to 12 carbon atoms such as phenyl, tolyl, xylyl, mesityl, naphtyl, and the like; camphor group, and the like.

The triphenylsulfonium salt of the formula (IVa) and diphenyliodonium salt of the formula (IVb) can be used as it is when it is commercially available, and also can be produced according to conventional methods.

The methods for producing triphenylsulfonium salt produced may be, for example, a method reacting corresponding triphenylsulfonium bromide with silver salt of sulfonic acid having the same structure of anion part of the intended sulfonium salt; a method reacting corresponding diphenylsulfoxide, aryl compound (i.e. diphenyl ether, diphenylsufoxide, and the like) and perfluoroalkanesulfonic acid in the presence of trifluoroacetic anhydride according to the method described in Chem. Pharm. Bull., Vol. 29, 3753 (1981); a method reacting corresponding aryl Grignard reagent with thionyl chloride, reacting the product with triorganosilyl halide to obtain triarylsulfonium halide, and then reacting the triarylsulfonium halide with silver salt of sulfonic acid having the same structure of anion part of the intended sulfonate according to the method described in JP-H08-311018-A; and the like. The sulfonium salt in which $P^1$, $P^2$ or $P^3$ in the formula (IVa) is hydroxy, can be produced by reacting triphenylsulfonium salt having tert-butoxy on its benzene ring with sulfonic acid having the same structure of anion part of the intended sulfonium salt to eliminate the tert-butyl according to the method described in JP-H08-311018-A.

The methods for producing diphenyliodonium salt of the formula (IVb) may be, for example, a method reacting iodosyl sulfate with corresponding aryl compound, and then adding thereto corresponding sulfonic acid having the same structure of anion part of the intended diphenyliodonium salt according to a method described in J. Am. Chem. Soc., vol. 81, 342 (1959); a method adding iodine and trifluoro acetic acid to a mixture of acetic anhydride and fuming nitric acid, then reacting the reaction mixture and corresponding aryl compound, and then adding thereto corresponding sulfonic acid having the same structure of anion part of the intended diphenyliodonium salt; a method reacting a mixture of corresponding aryl compound, acetic anhydride and potassium iodate by adding drop-wise concentrated sulfuric acid thereto, and then adding thereto corresponding sulfonic acid having the same structure of anion part of the intended diphenyliodonium salt according to a method described in JP-H09-179302-A; and the like.

Specific examples of the triphenylsulfonium salt of the formula (IVa) and the diphenyliodonium salt of the formula (IVb) include as follows:
triphenylsulfonium methanesulfonate,
triphenylsulfonium ethanesulfonate,
triphenylsulfonium butanesulfonate,
triphenylsulfonium perfluorobutanesulfonate,
triphenylsulfonium p-toluenesulfonate,
triphenylsulfonium camphorsulfonate,
4-methylphenyldiphenylsulfonium methanesulfonate,
4-methylphenyldiphenylsulfonium ethanesulfonate,
4-methylphenyldiphenylsulfonium butanesulfonate,
4-methylphenyldiphenylsulfonium benzenesulfonate,
4-methylphenyldiphenylsulfonium p-toluenesulfonate,
4-methylphenyldiphenylsulfonium camphorsulfonate,
4-methylphenyldiphenylsulfonium perfluorooctanesulfonate,
4-hydroxyphenyldiphenylsulfonium perfluorobutanesulfonate,
4-methoxyphenyldiphenylsulfonium perfluorobutanesulfonate,
tris(4-methylphenyl)sulfonium perfluorobutanesulfonate,
tris(4-methoxyphenyl)sulfonium perfluorobutanesulfonate,
4-hydroxyphenyldiphenylsulfonium perfluorooctanesulfonate,
4-methoxyphenyldiphenylsulfonium perfluorooctanesulfonate,
tris(4-methylphenyl)sulfonium perfluorooctanesulfonate,
tris(4-methoxyphenyl)sulfonium perfluorooctanesulfonate,
diphenyliodonium perfluorobutanesulfonate,
di(4-methoxyphenyl)iodonium perfluorooctanesulfonate,
di(4-tert-butylphenyl)iodonium perfluorooctanesulfonate,
di(4-tert-butylphenyl)iodonium methanesulfonate,
di(4-tert-butylphenyl)iodonium ethanesulfonate,
di(4-tert-butylphenyl)iodonium butanesulfonate,
di(4-tert-butylphenyl)iodonium benzenesulfonate,
di(4-tert-butylphenyl)iodonium p-toluenesulfonate,
di(4-tert-butylphenyl)iodonium camphorsulfonate, When at least one onium salt selected from the group consisting of triphenylsulfonium salt of the formula (IVa) and diphenylsulfonium salt of the formula (IVb) is contained in the present composition, the ratio of the onium salt in the total amount of the acid generator is usually from 10 to 500% by mol. The total amount of the acid generator means the amount of at least one onium salt selected from the group consisting of triphenylsulfonium salt of the formula (IVa) and diphenylsulfonium salt of the formula (IVb) and the amount of at least one acid generator selected from the group consisting of Salt (Ia), Polymer (Ib) and Salt (Ic)).

Next, resin components constituting the present composition will be explained. The resin used in the present composition contains a structural unit having an acid-labile group and the resin is insoluble or poorly soluble itself in alkali aqueous solution and shows partial dissociation of groups by the action of an acid to become soluble in alkali aqueous solution after the dissociation. The acid-labile group can be selected from conventionally known various groups.

Specifically, various carboxylate groups (—COOR) are mentioned as the acid-labile group, and examples thereof include alky carboxylate groups such as methyl carboxylate group and tert-butyl carboxylate group; acetal type carboxylate groups such as methoxymethyl carboxylate group, ethoxymethyl carboxylate group, 1-ethoxyethyl carboxylate group, 1-isobutoxyethyl carboxylate group, 1-isopropoxyethyl carboxylate group, 1-ethoxypropyl carboxylate group, 1-(2-methoxyethoxy)ethyl carboxylate group, 1-(2-acetoxyethoxy)ethyl carboxylate group, 1-[2-(1-adamantyloxy)ethoxy]ethyl carboxylate group, 1-[2-(1-adamantanecarbonyloxy)ethoxy]ethyl carboxylate group, tetrahydro-2-furyl carboxylate group and tetrahydro-2-pyranyl carboxylate group; alicyclic esters such as isobornyl carboxylate group, 2-alkyl-2-adamantyl carboxylate group, 1-(1-adamantyl)-1-alkylalkyl carboxylate group, and the like.

Monomers to be derived into structural units having such carboxylate group (—COOR) may be (meth)acryl-based monomers such as methacrylates and acrylates, or those obtained by bonding of a carboxylate group to alicyclic monomer such as norbornenecarboxylate, tricyclodecenecarboxylate and tetracyclodecenecarboxylate.

Among the above-mentioned monomers, it is preferable to use those having a bulky group containing alicyclic group such as, for example, 2-alkyl-2-adamantyl and 1-(1-adamantyl)-1-alkylalkyl, as the group dissociated by the action of an acid, since excellent resolution is obtained when used in the present composition.

Examples of such monomer containing a bulky group include 2-alkyl-2-adamantyl(meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene-2-carboxylate, and the like.

Particularly when 2-alkyl-2-adamantyl(meth)acrylate or 2-alkyl-2-adamantyl α-chloroacrylate is used as the monomer for the resin component in the present composition, excellent resolution is obtained. Typical examples of such 2-alkyl-2-adamantyl(meth)acrylate and 2-alkyl-2-adamantyl α-chloroacrylate include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate, 2-ethyl-2-adamantyl α-chloroacrylate and the like. When particularly 2-ethyl-2-adamantyl(meth)acrylate or 2-ethyl-2-adamantyl α-chloroacrylate is used for the present composition, balance between sensitivity and heat resistance is excellent. In the present invention, two or more kind of monomers having group dissociated by the action of an acid may be used together, if necessary.

2-alkyl-2-adamantyl(meth)acrylate can usually be produced by reacting 2-alkyl-2-adamantanol or metal salt thereof with an acrylic halide or methacrylic halide. 2-alkyl-2-adamantyl α-chloroacrylate can usually be produced by reacting 2-alkyl-2-adamantanol or metal salt thereof with an α-chloroacrylic halide.

The resin used for the present composition can also contain, in addition to the above-mentioned structural units having an acid-labile group, other structural units not dissociated or not easily dissociated by the action of an acid. Examples of such other structural units which can be contained include structural units derived from monomers having a free carboxyl group such as acrylic acid and methacrylic acid, structural units derived from aliphatic unsaturated dicarboxylic anhydrides such as maleic anhydride and itaconic anhydride, structural unit derived from 2-norbornene, structural unit derived from (meth)acrylonitrile, and the like.

In the case of KrF exposure, there is no problem on light absorption, and a structural unit derived from hydroxystyrene can be further contained.

Particularly, to contain, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl(meth)acrylate, a structural unit derived from 3,5-dihydroxy-1-adamantyl(meth)acrylate, a structural unit derived from (meth)acryloyloxy-γ-butyrolactone having a lactone ring optionally substituted by alkyl, a structural unit of the following formula (IIIa) and a structural unit of the following formula (IIIb), in the resin in the present composition, is preferable from the standpoint of the adhesiveness of resist to a substrate.

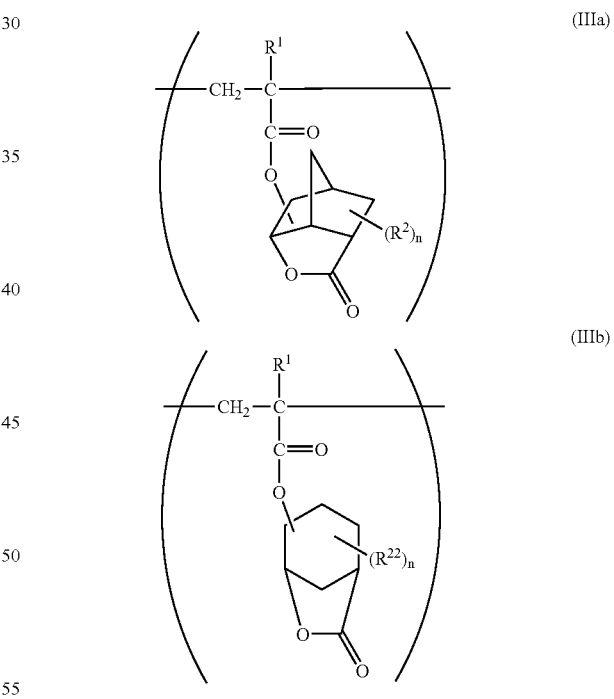

In the formulae (IIIa) and (IIIb), $R^1$ and $R^{21}$ each independently represent hydrogen, methyl or trifluoromethyl, and $R^2$ and $R^{22}$ each independently represent methyl or trifluoromethyl, and n represents an integer of from 1 to 3.

3-Hydroxy-1-adamantyl(meth)acrylate and 3,5-dihydroxy-1-adamantyl (meth)acrylate can be produced by, for example, reacting corresponding hydroxyadamantane with (meth)acrylic acid or its acid halide, and they are also commercially available.

Further, (meth)acryloyloxy-γ-butyrolactone can be produced by reacting α- or β-bromo-γ-butyrolactone having a lactone ring optionally substituted by alkyl with acrylic acid or methacrylic acid, or reacting α- or β-bromo-γ-butyrolactone having a lactone ring optionally substituted by alkyl with acrylic halide or methacrylic halide.

As monomers to be derived into structural units of the formulae (IIIa) and (IIIb), specifically listed are, for example, (meth)acrylates of alicyclic lactones having hydroxyl described below, and mixtures thereof, and the like. These esters can be produced, for example, by reacting corresponding alicyclic lactone having hydroxyl with (meth)acrylic acids, and the production method thereof is described in, for example, JP2000-26446-A.

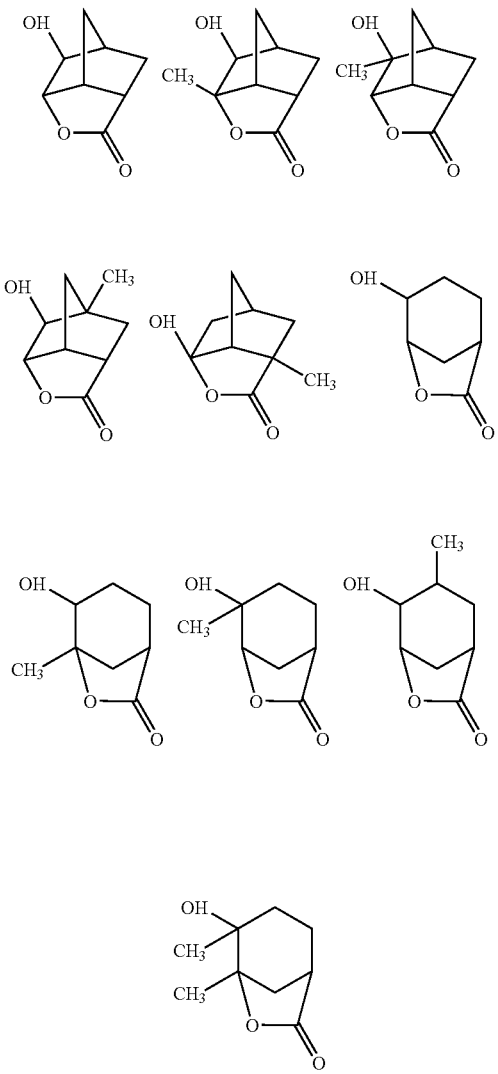

When any of the structural unit derived from 3-hydroxy-1-adamantyl (meth)acrylate, the structural unit derived from 3,5-dihydroxy-1-adamantyl (meth)acrylate, the structural unit derived from α-(meth)acryloyloxy-γ-butyrolactone, the structural unit derived from β-(meth)acryloyloxy-γ-butyrolactone and the structural unit of the formulae (IIIa) and (IIIb) is contained in the resin, not only the adhesiveness of the resist to a substrate is improved, but also the resolution of the resist is improved.

Here, examples of the (meth)acryloyloxy-γ-butyrolactone include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, β-methacryloyloxy-α-methyl-γ-butyrolactone and the like.

In the case of KrF excimer laser exposure, sufficient transmittance can be obtained even the structural unit derived from hydroxystyrene is contained in the resin. Specifically, copolymerization resins containing a structural unit derived from p- or m-hydroxystyrene as described below are listed. For obtaining such copolymerization resins, the corresponding (meth)acrylic ester monomer can be radical-polymerized with acetoxystyrene and styrene, and then the reaction mixture can be de-acetylated with an acid.

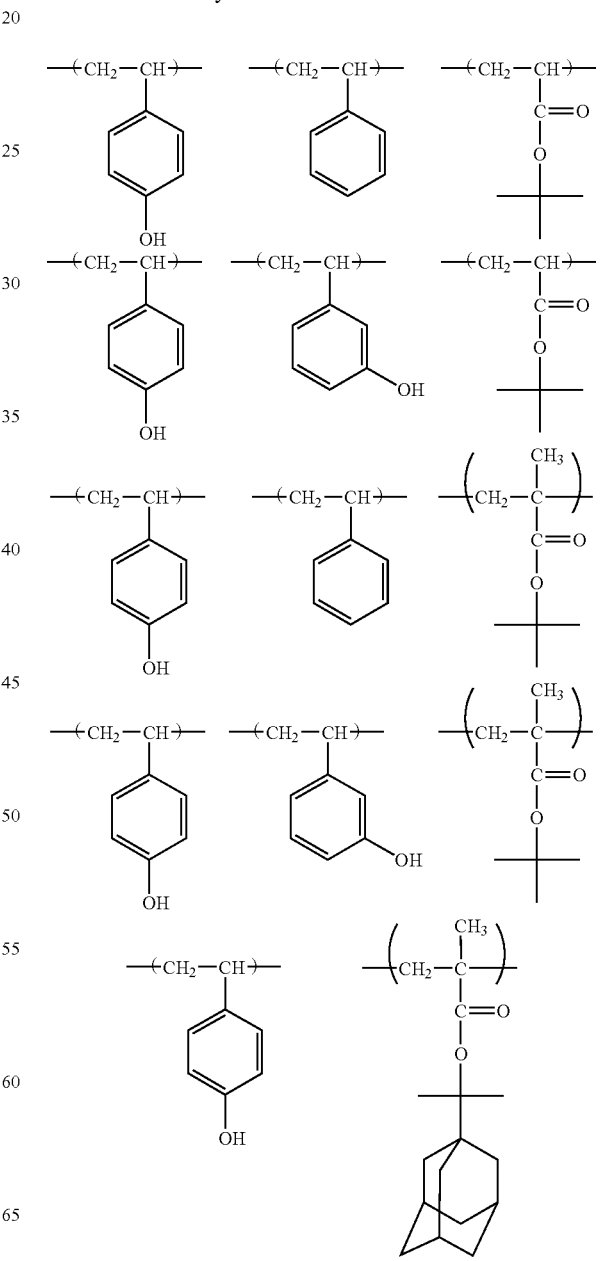

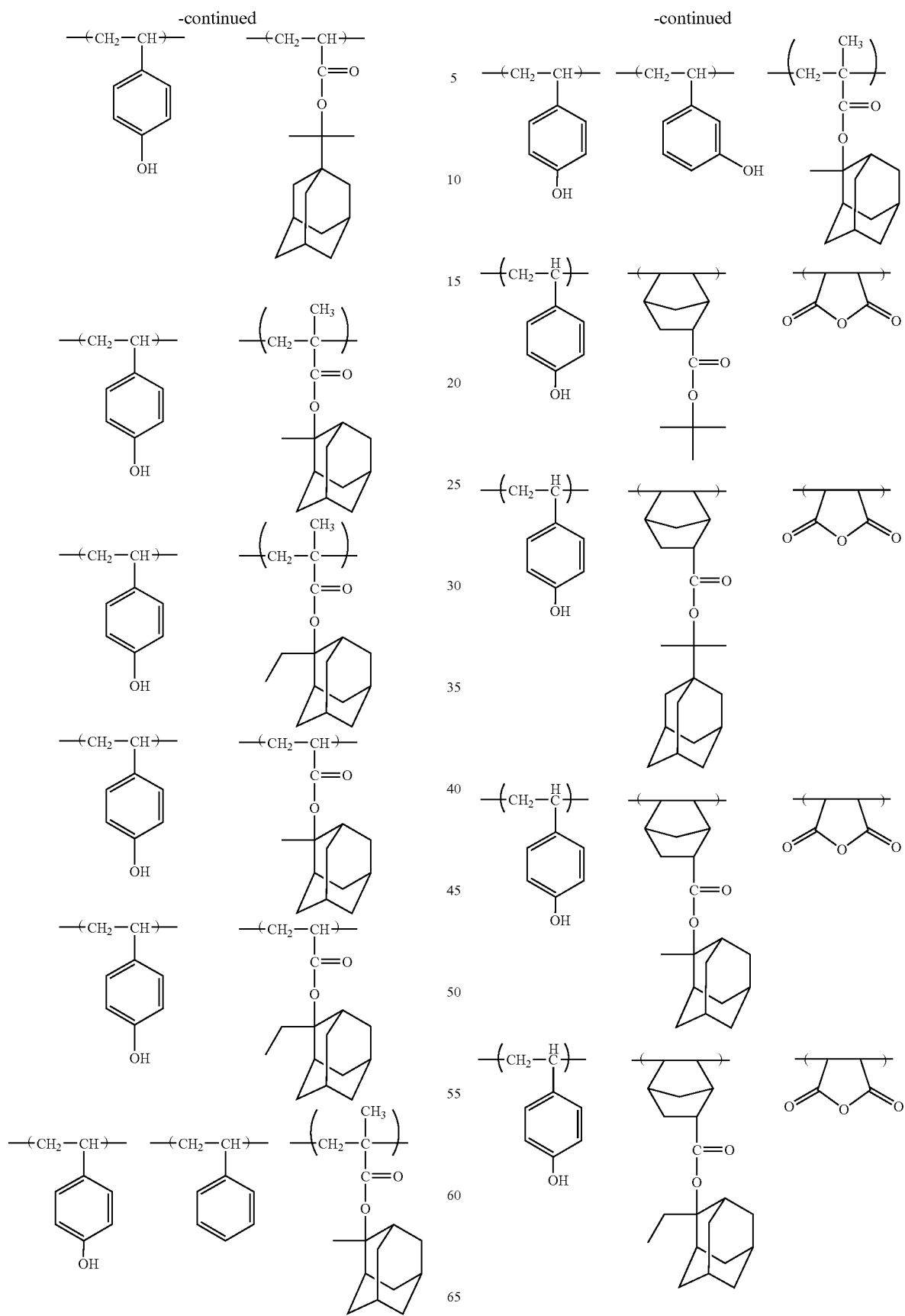

In these cases, it is advantageous from the standpoint of dry etching resistance to contain 2-alkyl-2-adamantyl or 1-(1-adamantyl)-1-alkylalkyl as the acid labile group in the resin.

The resin containing a structural unit derived from 2-norbornene shows strong structure because of alicyclic group directly present on its main chain and shows a property that dry etching resistance is excellent. The structural unit derived from 2-norbornene can be introduced into the main chain by radical polymerization using, for example, in addition to corresponding 2-norbornene, aliphatic unsaturated dicarboxylic anhydrides such as maleic anhydride and itaconic anhydride together. The structural unit derived from 2-norbornene is formed by opening of its double bond, and can be represented by the formula (VI). The structural unit derived from maleic anhydride and the structural unit derived from itaconic anhydride which are the structural unit derived from aliphatic unsaturated dicarboxylic anhydrides are formed by opening of their double bonds, and can be represented by the formula (VII) and the formula (VIII), respectively.

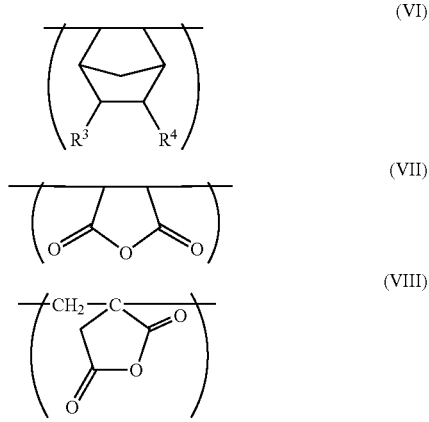

Here, $R^3$ and $R^4$ in the formula (VI) each independently represent hydrogen, alkyl having 1 to 3 carbon atoms, hydroxyalkyl having 1 to 3 carbon atoms, carboxyl, cyano or —COOG group in which G represents alcohol residue, or $R^3$ and $R^4$ can bond together to form a carboxylic anhydride residue represented by —C(=O)OC(=O)—.

In $R^3$ and $R^4$, examples of the alkyl include methyl, ethyl, propyl and isopropyl, specific examples of hydroxyalkyl include hydroxymethyl, 2-hydroxyethyl and the like.

In $R^3$ and $R^4$, —COOG group is an ester formed from carboxyl, and as the alcohol residue corresponding to G, for example, optionally substituted alkyls having about 1 to 8 carbon atoms, 2-oxooxolan-3- or -4-yl and the like are listed, and as the substituent on the alkyl, hydroxyl, alicyclic hydrocarbon residues and the like are listed.

Specific examples of —COOG include methoxycarbonyl, ethoxycarbonyl, 2-hydroxyethoxycarbonyl, tert-butoxycarbony, 2-oxooxalan-3-yloxycarbonyl, 2-oxooxalan-4-yloxycarbonyl, 1,1,2-trimethylpropoxycarbonyl, 1-cyclohexyl-1-methylethoxycarbonyl, 1-(4-methylcyclohexyl)-1-methylethoxycarbonyl, 1-(1-adamantyl)-1-methylethoxycarbonyl and the like.

Specific examples of the monomer used to derive the structural unit represented by the formula (VI) may include the followings;

2-norbornene,
2-hydroxy-5-norbornene,
5-norbornen-2-carboxylic acid,
methyl 5-norbornen-2-carboxylate,
t-butyl 5-norbornen-2-carboxylate,
1-cyclohexyl-1-methylethyl 5-norbornen-2-carboxylate,
1-(4-methylcyclohexyl)-1-methylethyl 5-norbornen-2-carboxylate,
1-(4-hydroxycyclohexyl)-1-methylethyl 5-norbornen-2-carboxylate,
1-methyl-1-(4-oxocyclohexyl)ethyl 5-norbornen-2-carboxylate,
1-(1-adamantyl)-1-methylethyl 5-norbornen-2-carboxylate,
1-methylcyclohexyl 5-norbornen-2-carboxylate,
2-methyl-2-adamantyl 5-norbornen-2-carboxylate,
2-ethyl-2-adamantyl 5-norbornen-2-carboxylate,
2-hydroxyethyl 5-norbornen-2-carboxylate,
5-norbornen-2-methanol,
5-norbornen-2,3-dicarboxylic acid anhydride, and the like.

The resin used in the present composition preferably contains structural unit(s) having an acid-labile group generally in a ratio of 10 to 80% by mol in all structural units of the resin though the ratio varies depending on the kind of radiation for patterning exposure, the kind of an acid-labile group, and the like.

When the structural units particularly derived from 2-alkyl-2-adamantyl (meth)acrylate or 1-(1-adamantyl)-1-alkylalkyl(meth)acrylate are used as the acid-labile group, it is advantageous that the ratio of the structural units is 15% by mol or more in all structural units of the resin.

When, in addition to structural units having an acid-labile group, other structural units not easily dissociated by the action of an acid, for example, a structural unit derived from 3-hydroxy-1-adamantyl(meth)acrylate, a structural units derived from 3,5-dihydroxy-1-adamantyl(meth)acrylate or α-(meth)acryloyloxy-γ-butyrolactone, a structural units derived from β-(meth)acryloyloxy-γ-butyrolactone, a structural unit of the formula (IIIa) or (IIIb), a structural unit derived from hydroxystyrene, a structural unit of the formula (VI), a structural unit derived from maleic anhydride of the formula (VII) which is a structural unit derived from an aliphatic unsaturated dicarboxylic anhydride, a structural unit derived from itaconic anhydride of the formula (VIII) and the like are contained, it is preferable that the sum of these structural units is in the range of 20 to 90% by mol based on all structural units of the resin.

When 2-norbornenes and aliphatic unsaturated dicarboxylic anhydride are used as copolymerization monomer, it is preferable to use them in excess amount in view of a tendency that these are not easily polymerized.

In the present composition, performance deterioration caused by inactivation of acid which occurs due to post exposure delay can be diminished by adding basic compounds, particularly, basic nitrogen-containing organic compounds, for example, amines as a quencher.

Specific examples of such basic nitrogen-containing organic compounds include the ones represented by the following formulae:

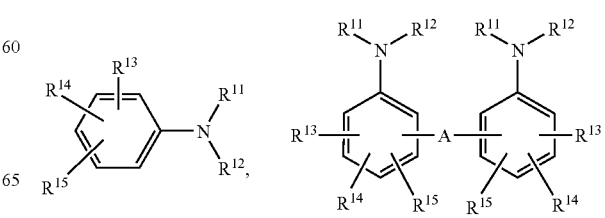

-continued

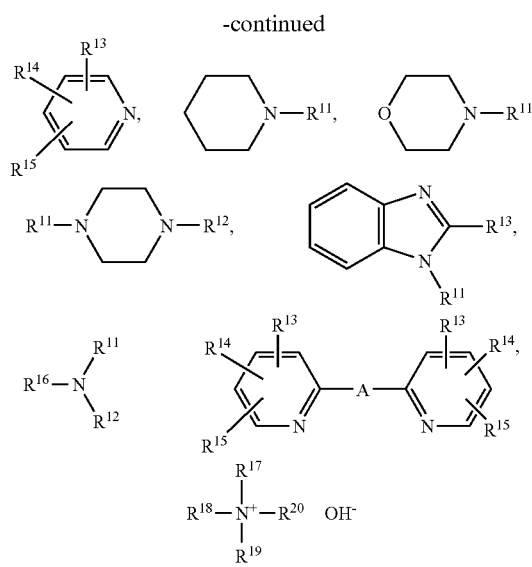

Wherein $R^{11}$ and $R^{12}$ represent each independently hydrogen, alkyl, cycloalkyl or aryl. The alkyl preferably has about 1 to 6 carbon atoms, the cycloalkyl preferably has about 5 to 10 carbon atoms, and the aryl preferably has about 6 to 10 carbon atoms. Furthermore, at least one hydrogen on the alkyl, cycloalkyl or aryl may each independently be substituted by hydroxyl, amino, or alkoxy having 1 to 6 carbon atoms. At least one hydrogen on the amino may each independently be substituted by alkyl having 1 to 4 carbon atoms.

$R^{13}$, $R^{14}$ and $R^{15}$ each independently represent hydrogen, alkyl, cycloalkyl, aryl or alkoxy. The alkyl preferably has about 1 to 6 carbon atoms, the cycloalkyl preferably has about 5 to 10 carbon atoms, the aryl preferably has about 6 to 10 carbon atoms, and the alkoxy preferably has about 1 to 6 carbon atoms. Furthermore, at least one hydrogen on the alkyl, cycloalkyl, aryl or alkoxy may each independently be substituted by hydroxyl, amino, or alkoxy having 1 to 6 carbon atoms. At least one hydrogen on the amino may be substituted by alkyl having 1 to 4 carbon atoms.

$R^{16}$ represents alkyl or cycloalkyl. The alkyl preferably has about 1 to 6 carbon atoms, and the cycloalkyl preferably has about 5 to 10 carbon atoms. Furthermore, at least one hydrogen on the alkyl or cycloalkyl may each independently be substituted by hydroxyl, amino, or alkoxy having 1 to 6 carbon atoms. At least one hydrogen on the amino may be substituted by alkyl having 1 to 4 carbon atoms.

$R^{17}$, $R^{18}$, $R^{19}$ and $R^{20}$ each independently represent alkyl, cycloalkyl or aryl. The alkyl preferably has about 1 to 6 carbon atoms, the cycloalkyl preferably has about 5 to 10 carbon atoms, and the aryl preferably has about 6 to 10 carbon atoms. Furthermore, at least one hydrogen on the alkyl, cycloalkyl or aryl may each independently be substituted by hydroxyl, amino, or alkoxy having 1 to 6 carbon atoms. At least one hydrogen on the amino may each independently be substituted by alkyl having 1 to 4 carbon atoms.

A represents alkylene, carbonyl, imino, sulfide or disulfide. The alkylene preferably has about 2 to 6 carbon atoms.

Moreover, among $R^{11}$-$R^{20}$, in regard to those which can be straight-chained or branched, either of these may be permitted.

Examples of such compounds include hexylamine, heptylamine, octylamine, nonylamine, decylamine, aniline, 2-, 3- or 4-methylaniline, 4-nitroaniline, 1- or 2-naphtylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-isopropylaniline, imidazole, pyridine, 4-methylpyridine, 4-methylmidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-trifluoromethylphenyltrimethylammonium hydroxide, (2-hydroxyethyl)trimethylammonium hydroxide (so-called "choline"), and the like.

Furthermore, hindered amine compounds having piperidine skeleton as disclosed in JP-A-H11-52575 can be used as quencher.

It is preferable that the present composition contains resin in an amount of about 80 to 99.9% by weight and the acid generator in a total amount of 0.1 to 20% by weight based on the total solid content of the present composition.

When basic compound is used as a quencher, it is preferable that the basic compound is contained in an amount of about 0.01 to 1% by weight based on the total solid content of the present composition.

The present composition can contain, if necessary, various additives in small amount such as a sensitizer, solution suppressing agent, other resins, surfactant, stabilizer, dye and the like, as long as the effect of the present invention is not prevented.

The present composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used. In the present invention, the total solid content means total content exclusive of solvents.

Examples thereof include glycol ether esters such as ethylcellosolve acetate, methylcellosolve acetate and propylene glycol monomethyl ether acetate; esters such as ethyl lactate, butyl lactate, amyl lactate and ethyl pyruvate and the like; ketones such as acetone, methyl isobutyl ketone, 2-heptanone and cyclohexanone; cyclic esters such as γ-butyrolactone, and the like. These solvents can be used each alone or in combination of two or more.

A resist film applied onto the substrate and then dried is subjected to exposure for patterning, then heat-treated for facilitating a deblocking reaction, and thereafter developed with an alkali developer. The alkali developer used here may be any one of various alkaline aqueous solutions used in the art, and generally, an aqueous solution of tetramethylammonium hydroxide or (2-hydroxyethyl)trimethylammonium hydroxide (commonly known as "choline") is often used.

The present invention will be described more specifically by way of examples, which are not construed to limit the scope of the present invention. The "%" and "part(s)" used to represent the content of any component and the amount of any material used in the following examples are on a weight basis unless otherwise specifically noted. The weight-average molecular weight of any material used in the following examples is a value found by gel permeation chromatography using styrene as a standard reference material.

ACID GENERATOR SYNTHESIS EXAMPLE 1

Synthesis of Acid Generator B1

(1) Into a four-necked flask was charged 25.89 parts of 2-hydroxyethyl methacrylate, 39.46 parts of N-methylpiperidine and 129.46 parts of methyl isobutyl ketone, and into this was dropped 64.25 parts of bromoacetyl bromide and the mixture was stirred at 50° C. for 24 hours. To this was added 100 parts of methyl isobutyl ketone and 100 parts of ion exchanged water, then, the solution was mixed and phase-separated. The organic phase obtained by the phase-separation was washed three time with each of 100 parts of ion exchanged water, 100 parts of 5% potassium carbonate and 100 parts of ion exchanged water. Then, the solution was concentrated, and purified by silica gel column chromatography, to obtain 21.94 parts of a concentrated intermediate bromide.

(2) Into a four-necked flask was charged 14.34 parts of tetrahydrothiophene and 50 parts of acetone, and then, 10.00 parts of the intermediate bromide obtained in (1) was dropped into this, the mixture was stirred, then, 13.47 parts of potassium perfluorobutanesulfonate was added and the mixture was stirred for 24 hours. The deposited solid was filtrated out, then, the solution was concentrated, and purified by silica gel column chromatography and the product was concentrated to obtain 14.38 parts of the intended product. This compound was confirmed to be 1-[2-(2-methylacryloyloxy)ethoxycarbonyl]tetrahydrothiophenium perfluorobutanesulfonate by NMR ("GX-270" manufactured by JEOL Ltd.).

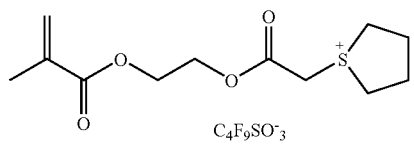

$^1$H-NMR (dimethyl sulfoxide-$d_6$, internal standard substance:tetramethylsilane): δ (ppm) 1.91 (s, 3H); 2.20-2.30 (m, 4H); 3.57-3.71 (m, 4H); 4.36-4.39 (m, 2H); 4.45-4.49 (m, 2H); 4.57 (s, 2H); 5.73-5.74 (m, 1H); 6.00 (s, 1H), $^{19}$F-NMR (dimethyl sulfoxide-$d_6$, external standard substance: hexafluorobenzene): δ (ppm)-85.71 (s, 3F); 119.81 (s, 2F); 126.41 (s, 2F); 130.81 (s, 2F).

ACID GENERATOR SYNTHESIS EXAMPLE 2

Synthesis of Acid Generator B2

Into a four-necked flask was charged 6.0 g of dioxane which had been deaerated with nitrogen and it was heated to 58° C., and a mixed solution of 5.0 g of the acid generator B1 shown in Acid generator Synthesis Example 1, 0.1 g of azobisisobutyronitrile as an initiator and 9.0 g of dioxane was dropped. Then, the mixture was heated at 58° C. for about 11 hours. Then, the reaction liquid was returned to room temperature, then, the solvent was removed under reduced pressure, to obtain a homopolymer having the following structural unit in a yield of 80%. Polymerization was confirmed by a fact that a peak in $^1$H-NMR was broad. This is called acid generator B2.

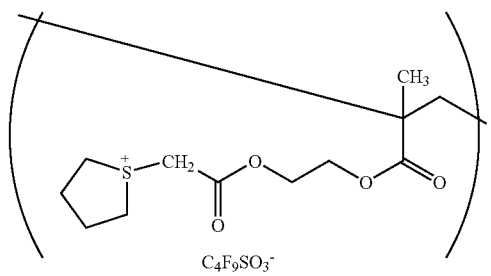

ACID GENERATOR SYNTHESIS EXAMPLE 3

Synthesis of Acid Generator B3

(1) Into a four-necked flask was charged 70.17 parts of tetrahydrothiophene and 750 parts of acetone, into this was dropped 150 parts of 1-bromopinacolone, and the mixture was stirred at room temperature for 24 hours. The deposited crystal was filtrated and washed with 100 parts of tert-butyl methyl ether and dried to obtain 161.3 parts of 3,3-dimethyl-2-oxobutyl thiacyclopentanium bromide.

(2) Into a four-necked flask was charged 80 parts of 3,3-dimethyl-2-oxobutyl thiacyclopentanium bromide and 3200 parts of acetonitrile, and into this was dropped 101 parts of potassium perfluorobutanesulfonate, and the mixture was stirred at room temperature for 18 hours. The deposited potassium bromide was filtrated off, and the filtrate was concentrated. To this was added acetone and stirred at room temperature for 16 hours, and insoluble substances were filtrated off. The filtrate was further concentrated, acetone was added to this and the mixture was charged into tert-butyl methyl ether, to obtain 137 parts of the intended product. This compound was confirmed to be 3,3-dimethyl-2-oxobutyl thiacyclopentanium perfluorobutanesulfonate by $^1$H-NMR ("GX-270" manufactured by JEOL Ltd.).

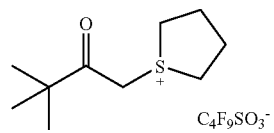

$^1$H-NMR (dimethyl sulfoxide-$d_6$, internal standard substance:tetramethylsilane) of 3,3-dimethyl-2-oxobutyl thiacyclopentanium perfluorobutanesulfonate: δ (ppm) 1.15 (s, 9H); 2.13-2.23 (m, 4H); 3.33-3.38 (m, 2H); 3.47-3.54 (m, 2H); 4,85 (s, 2H).

RESIN SYNTHESIS EXAMPLE 1 (SYNTHESIS OF RESIN A1)

2-Ethyl-2-adamantyl methacrylate, 3-hydroxy-1-adamantyl methacrylate and α-methacryloyloxy-γ-butyrolactone were charged at a molar ratio of 5:2.5:2.5 (20.0 parts:9.5 parts:7.3 parts), and methyl isobutyl ketone in twice weight based on all monomers was added, to prepare solution. To the solution was added azobisisobutyronitrile as an initiator in a ratio of 2 mol % based on all monomer molar amount, and the mixture was heated at 80° C. for about 8 hours. Then, the reaction solution was poured into large amount of heptane to cause precipitation, and this operation was repeated three times for purification. As a result, copolymer having a weight-average molecular weight of about 9,200 was obtained. This is called resin A1.

Resin A2: Copolymer derived from 2-methyl-2-adamantyl methacrylate and α-methacryloxy-γ-butyrolactone (50:50) (IHM55-10K, produce by Mitsubishi rayon Co., Ltd.)

EXAMPLES 1 TO 3 AND COMPARATIVE EXAMPLES 1 TO 3

The resin and the acid generator shown in Table 2 were mixed with the following components and dissolved to obtain a solution. The solution was filtrated through a fluorine resin filter having pore diameter of 0.2 μm, to prepare resist liquid.

<Acid Generator> (The kind and amount are described in Table 1.)

Acid Generator B1:
1-[2-(2-methyl-acryloyloxy)-ethoxycarbonyl]-tetrahydrothiophenium trifluoromethanesulfonate Acid Generator B2:
1-[2-(2-methyl-acryloyloxy)-ethoxycarbonyl]-tetrahydrothiophenium trifluorobutanesulfonate Acid Generator B3:
3,3-dimethyl-2-oxobutylthiacyclopentanium perfluorooctanesulfonate Acid Generator C1:
4-methylphenyldiphenylsulfonium perfluorooctanesulfonate Acid Generator C2:
4-methylphenyldiphenylsulfonium perfluorobutanesulfonate <Resin>10 parts (The kind is described in Table 1.)

Resin A1: Produced in Resin Synthesis Example 1

Resin A2: Copolymer derived from 2-methyl-2-adamantyl methacrylate and α-methacryloxy-γ-butyrolactone (50:50) (IHM55-10K, produce by Mitsubishi rayon Co., Ltd.)

| <Quencher> | |
|---|---|
| 2,6-diisopropylaniline | 0.0075 part |

| <Solvent> | |
|---|---|
| propylene glycol monomethyl ether acetate | 85.4 parts |
| γ-butyrolactone | 4.5 parts |
| γ-butyrolactone | 3.5 parts |

Silicon wafers were each coated with "ARC-29A", which is an organic anti-reflective coating composition available from Brewer Co., and then baked under the conditions: 215° C., 60 seconds, to form a 780 Å-thick organic anti-reflective coating. Each of the resist liquids prepared as above was spin-coated over the anti-reflective coating so that the thickness of the resulting film became 0.335 μm after drying. The silicon wafers thus coated with the respective resist liquids were each prebaked on a direct hotplate at temperature shown in "PB" column in Table 1 for 60 seconds. Using an ArF excimer stepper ("NSR ArF" manufactured by Nikon Corporation, NA=0.55, 2/3 Annular), each wafer thus formed with the respective resist film was subjected to line and space pattern exposure, with the exposure quantity being varied stepwise.

After the exposure, each wafer was subjected to post-exposure baking on a hotplate at temperature shown in "PEB" column in Table 1 for 60 seconds and then to paddle development for 60 seconds with an aqueous solution of 2.38 wt % tetramethylammonium hydroxide.

The pattern developed on the organic anti-reflective coating substrate was observed with a scanning electron microscope, effective sensitivity and resolution thereof were checked. The results are shown in Table 2.

Effective sensitivity: It is expressed as the amount of exposure that the line pattern (light-shielding layer) and the space pattern (light-transmitting layer) become 1:1 after exposure through 0.13 μm line and space pattern mask and development.

Resolution: It is expressed as the minimum size of space pattern which gave the space pattern split by the line pattern at the exposure amount of the effective sensitivity.

TABLE 1

| Example No. | Resin | Acid Generator/Part | PB | PEB |
|---|---|---|---|---|
| Example 1 | A1 | B1/0.5 + C1/0.2 | 130° C. | 120° C. |
| Example 2 | A2 | B1/0.5 + C2/0.2 | 110° C. | 110° C. |
| Example 3 | A2 | B2/0.5 + C2/0.2 | 110° C. | 110° C. |
| Comparative Example 1 | A1 | B3/0.5 + C1/0.2 | 130° C. | 120° C. |
| Comparative Example 2 | A1 | C1/0.5 | 110° C. | 110° C. |
| Comparative Example 3 | A2 | C1/0.2 | 110° C. | 110° C. |

TABLE 2

| Example No. | Effective Sensitivity (mJ/cm$^2$) | Resolution (μm) | Collape Starting Size of Pattern | Smoothness of Pattern Wall |
|---|---|---|---|---|
| Example 1 | 22.5 | 0.12 | 0.12 | ○ |
| Example 2 | 24.0 | 0.12 | <0.12 | ○ |
| Example 3 | 25.5 | 0.12 | <0.12 | ○ |
| Comparative Example 1 | 24 | 0.13 | 0.14 | |
| Comparative Example 2 | 45 | 0.13 | 0.15 | |
| Comparative Example 3 | 44 | 0.12 | 0.14 | |

The chemical amplification type resist composition of the present invention provides fine patterns without collapse, and gives excellent various resist properties such as. Therefore, it is suitable for excimer laser lithography using ArF or KrF.

What is claimed is:

1. A polymeric compound comprising a structural unit of the formula (Ib)

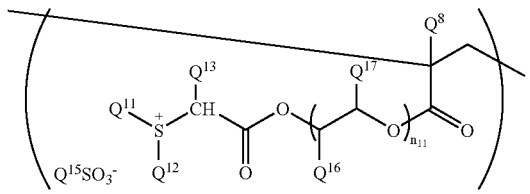

wherein $Q^{11}$ and $Q^{12}$ each independently represent alkyl having 1 to 6 carbon atoms or cycloalkyl having 3 to 10 carbon atoms, or $Q^{11}$ and $Q^{12}$ bond to form divalent acyclic hydrocarbon having 3 to 7 carbon atoms which form a ring together with the adjacent $S^+$; $Q^8$, $Q^{13}$, $Q^{16}$ and $Q^{17}$ each independently represent hydrogen or methyl; $n_{11}$ denotes 0 or natural number; and $Q^{15}$ represents perfluoroalkyl having 1 to 8 carbon atoms, alkyl having 1 to 8 carbon atoms or aromatic group having 6 to 12 carbon atoms which may be substituted, or camphor group.

2. The polymeric compound according to claim 1, wherein $Q^{11}$ and $Q^{12}$ each independently represent alkyl having 1 to 4 carbon atoms or $Q^{11}$ and $Q^{12}$ bond to form divalent acyclic hydrocarbon having 4 to 5 carbon atoms which form a ring together with the adjacent $S^+$.

3. The polymeric salt according to claim 1, wherein $n_{11}$ in the formula (1b) is 0 to 3.

* * * * *